(12) United States Patent
Mire et al.

(10) Patent No.: US 7,835,784 B2
(45) Date of Patent: Nov. 16, 2010

(54) METHOD AND APPARATUS FOR POSITIONING A REFERENCE FRAME

(75) Inventors: David A. Mire, Cordova, TN (US); John B. Clayton, Superior, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1051 days.

(21) Appl. No.: 11/232,445

(22) Filed: Sep. 21, 2005

(65) Prior Publication Data

US 2007/0066887 A1    Mar. 22, 2007

(51) Int. Cl.
*A61B 5/05* (2006.01)
(52) U.S. Cl. .................. 600/424; 600/407; 600/429
(58) Field of Classification Search ............... 600/407, 600/424, 595, 429; 606/53
See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |

(Continued)

FOREIGN PATENT DOCUMENTS

CA    964149    3/1975

(Continued)

OTHER PUBLICATIONS

Adams et al., Computer-Assisted Surgery, IEEE Computer Graphics & Applications, pp. 43-51, (May 1990).

(Continued)

*Primary Examiner*—Eric F Winakur
*Assistant Examiner*—Katherine L Fernandez
(74) *Attorney, Agent, or Firm*—Harness, Dickey

(57) ABSTRACT

A method and apparatus to perform a procedure that can include a processor assisted surgical procedure. During the procedure patient space and image space can be registered to allow for tracking of various tracking sensors. A dynamic reference frame can be used to maintain localization of the patient space with the image space. The dynamic reference frame can be fixedly interconnected with a bone portion of the anatomy.

61 Claims, 8 Drawing Sheets

U.S. PATENT DOCUMENTS

| | | | |
|---|---|---|---|
| 4,037,592 A | 7/1977 | Kronner | |
| 4,052,620 A | 10/1977 | Brunnett | |
| 4,054,881 A | 10/1977 | Raab | |
| 4,117,337 A | 9/1978 | Staats | |
| 4,173,228 A | 11/1979 | Van Steenwyk et al. | |
| 4,182,312 A | 1/1980 | Mushabac | |
| 4,202,349 A | 5/1980 | Jones | |
| 4,228,799 A | 10/1980 | Anichkov et al. | |
| 4,256,112 A | 3/1981 | Kopf et al. | |
| 4,262,306 A | 4/1981 | Renner | |
| 4,287,809 A | 9/1981 | Egli et al. | |
| 4,298,874 A | 11/1981 | Kuipers | |
| 4,314,251 A | 2/1982 | Raab | |
| 4,317,078 A | 2/1982 | Weed et al. | |
| 4,319,136 A | 3/1982 | Jinkins | |
| 4,328,548 A | 5/1982 | Crow et al. | |
| 4,328,813 A | 5/1982 | Ray | |
| 4,339,953 A | 7/1982 | Iwasaki | |
| 4,341,220 A | 7/1982 | Perry | |
| 4,346,384 A | 8/1982 | Raab | |
| 4,358,856 A | 11/1982 | Stivender et al. | |
| 4,368,536 A | 1/1983 | Pfeiler | |
| 4,396,885 A | 8/1983 | Constant | |
| 4,396,945 A | 8/1983 | DiMatteo et al. | |
| 4,403,321 A | 9/1983 | DiMarco | |
| 4,418,422 A | 11/1983 | Richter et al. | |
| 4,419,012 A | 12/1983 | Stephenson et al. | |
| 4,422,041 A | 12/1983 | Lienau | |
| 4,431,005 A | 2/1984 | McCormick | |
| 4,485,815 A | 12/1984 | Amplatz | |
| 4,506,676 A | 3/1985 | Duska | |
| 4,543,959 A | 10/1985 | Sepponen | |
| 4,548,208 A | 10/1985 | Niemi | |
| 4,571,834 A | 2/1986 | Fraser et al. | |
| 4,572,198 A | 2/1986 | Codrington | |
| 4,583,538 A | 4/1986 | Onik et al. | |
| 4,584,577 A | 4/1986 | Temple | |
| 4,608,977 A | 9/1986 | Brown | |
| 4,613,866 A | 9/1986 | Blood | |
| 4,617,925 A | 10/1986 | Laitinen | |
| 4,618,978 A | 10/1986 | Cosman | |
| 4,621,628 A | 11/1986 | Brudermann | |
| 4,625,718 A | 12/1986 | Olerud et al. | |
| 4,638,798 A | 1/1987 | Shelden et al. | |
| 4,642,786 A | 2/1987 | Hansen | |
| 4,645,343 A | 2/1987 | Stockdale et al. | |
| 4,649,504 A | 3/1987 | Krouglicof et al. | |
| 4,651,732 A | 3/1987 | Frederick | |
| 4,653,509 A | 3/1987 | Oloff et al. | |
| 4,659,971 A | 4/1987 | Suzuki et al. | |
| 4,660,970 A | 4/1987 | Ferrano | |
| 4,673,352 A | 6/1987 | Hansen | |
| 4,688,037 A | 8/1987 | Krieg | |
| 4,701,049 A | 10/1987 | Beckman et al. | |
| 4,705,395 A | 11/1987 | Hageniers | |
| 4,705,401 A | 11/1987 | Addleman et al. | |
| 4,706,665 A | 11/1987 | Gouda | |
| 4,709,156 A | 11/1987 | Murphy et al. | |
| 4,710,708 A | 12/1987 | Rorden et al. | |
| 4,719,419 A | 1/1988 | Dawley | |
| 4,722,056 A | 1/1988 | Roberts et al. | |
| 4,722,336 A | 2/1988 | Kim et al. | |
| 4,723,544 A | 2/1988 | Moore et al. | |
| 4,727,565 A | 2/1988 | Ericson | |
| RE32,619 E | 3/1988 | Damadian | |
| 4,733,969 A | 3/1988 | Case et al. | |
| 4,737,032 A | 4/1988 | Addleman et al. | |
| 4,737,794 A | 4/1988 | Jones | |
| 4,737,921 A | 4/1988 | Goldwasser et al. | |
| 4,742,356 A | 5/1988 | Kuipers | |
| 4,742,815 A | 5/1988 | Ninan et al. | |
| 4,743,770 A | 5/1988 | Lee | |
| 4,743,771 A | 5/1988 | Sacks et al. | |
| 4,745,290 A | 5/1988 | Frankel et al. | |
| 4,750,487 A | 6/1988 | Zanetti | |
| 4,753,528 A | 6/1988 | Hines et al. | |
| 4,761,072 A | 8/1988 | Pryor | |
| 4,764,016 A | 8/1988 | Johansson | |
| 4,771,787 A | 9/1988 | Wurster et al. | |
| 4,779,212 A | 10/1988 | Levy | |
| 4,782,239 A | 11/1988 | Hirose et al. | |
| 4,788,481 A | 11/1988 | Niwa | |
| 4,791,934 A | 12/1988 | Brunnett | |
| 4,793,355 A | 12/1988 | Crum et al. | |
| 4,794,262 A | 12/1988 | Sato et al. | |
| 4,797,907 A | 1/1989 | Anderton | |
| 4,803,976 A | 2/1989 | Frigg et al. | |
| 4,804,261 A | 2/1989 | Kirschen | |
| 4,805,615 A | 2/1989 | Carol | |
| 4,809,694 A | 3/1989 | Ferrara | |
| 4,821,200 A | 4/1989 | Öberg | |
| 4,821,206 A | 4/1989 | Arora | |
| 4,821,731 A | 4/1989 | Martinelli et al. | |
| 4,822,163 A | 4/1989 | Schmidt | |
| 4,825,091 A | 4/1989 | Breyer et al. | |
| 4,829,373 A | 5/1989 | Leberl et al. | |
| 4,836,778 A | 6/1989 | Baumrind et al. | |
| 4,838,265 A | 6/1989 | Cosman et al. | |
| 4,841,967 A | 6/1989 | Chang et al. | |
| 4,845,771 A | 7/1989 | Wislocki et al. | |
| 4,849,692 A | 7/1989 | Blood | |
| 4,860,331 A | 8/1989 | Williams et al. | |
| 4,862,893 A | 9/1989 | Martinelli | |
| 4,869,247 A | 9/1989 | Howard, III et al. | |
| 4,875,165 A | 10/1989 | Fencil et al. | |
| 4,875,478 A | 10/1989 | Chen | |
| 4,884,566 A | 12/1989 | Mountz et al. | |
| 4,889,526 A | 12/1989 | Rauscher et al. | |
| 4,896,673 A | 1/1990 | Rose et al. | |
| 4,905,698 A | 3/1990 | Strohl, Jr. et al. | |
| 4,923,459 A | 5/1990 | Nambu | |
| 4,931,056 A | 6/1990 | Ghajar et al. | |
| 4,945,305 A | 7/1990 | Blood | |
| 4,945,914 A | 8/1990 | Allen | |
| 4,951,653 A | 8/1990 | Fry et al. | |
| 4,955,891 A | 9/1990 | Carol | |
| 4,961,422 A | 10/1990 | Marchosky et al. | |
| 4,977,655 A | 12/1990 | Martinelli | |
| 4,989,608 A | 2/1991 | Ratner | |
| 4,991,579 A | 2/1991 | Allen | |
| 5,002,058 A | 3/1991 | Martinelli | |
| 5,005,592 A | 4/1991 | Cartmell | |
| 5,013,317 A | 5/1991 | Cole et al. | |
| 5,016,639 A | 5/1991 | Allen | |
| 5,017,139 A | 5/1991 | Mushabac | |
| 5,027,818 A | 7/1991 | Bova et al. | |
| 5,030,196 A | 7/1991 | Inoue | |
| 5,030,222 A | 7/1991 | Calandruccio et al. | |
| 5,031,203 A | 7/1991 | Trecha | |
| 5,042,486 A | 8/1991 | Pfeiler et al. | |
| 5,047,036 A | 9/1991 | Koutrouvelis | |
| 5,050,608 A | 9/1991 | Watanabe et al. | |
| 5,054,492 A | 10/1991 | Scribner et al. | |
| 5,057,095 A | 10/1991 | Fabian | |
| 5,059,789 A | 10/1991 | Salcudean | |
| 5,078,140 A | 1/1992 | Kwoh | |
| 5,079,699 A | 1/1992 | Tuy et al. | |
| 5,086,401 A | 2/1992 | Glassman et al. | |
| 5,094,241 A | 3/1992 | Allen | |
| 5,097,839 A | 3/1992 | Allen | |
| 5,098,426 A | 3/1992 | Sklar et al. | |
| 5,099,845 A | 3/1992 | Besz et al. | |
| 5,099,846 A | 3/1992 | Hardy | |
| 5,105,829 A | 4/1992 | Fabian et al. | |

| | | | | | |
|---|---|---|---|---|---|
| 5,107,839 A | 4/1992 | Houdek et al. | 5,330,485 A | 7/1994 | Clayman et al. |
| 5,107,843 A | 4/1992 | Aarnio et al. | 5,333,168 A | 7/1994 | Fernandes et al. |
| 5,107,862 A | 4/1992 | Fabian et al. | 5,353,795 A | 10/1994 | Souza et al. |
| 5,109,194 A | 4/1992 | Cantaloube | 5,353,800 A | 10/1994 | Pohndorf et al. |
| 5,119,817 A | 6/1992 | Allen | 5,353,807 A | 10/1994 | DeMarco |
| 5,142,930 A | 9/1992 | Allen et al. | 5,359,417 A | 10/1994 | Müller et al. |
| 5,143,076 A | 9/1992 | Hardy et al. | 5,368,015 A | 11/1994 | Wilk |
| 5,152,288 A | 10/1992 | Hoenig et al. | 5,368,030 A | 11/1994 | Zinreich et al. |
| 5,160,337 A | 11/1992 | Cosman | 5,371,778 A | 12/1994 | Yanof et al. |
| 5,161,536 A | 11/1992 | Vilkomerson et al. | 5,375,596 A | 12/1994 | Twiss et al. |
| 5,178,164 A | 1/1993 | Allen | 5,377,678 A | 1/1995 | Dumoulin et al. |
| 5,178,621 A | 1/1993 | Cook et al. | 5,383,454 A | 1/1995 | Bucholz |
| 5,186,174 A | 2/1993 | Schlondorff et al. | 5,385,146 A | 1/1995 | Goldreyer |
| 5,187,475 A | 2/1993 | Wagener et al. | 5,385,148 A | 1/1995 | Lesh et al. |
| 5,188,126 A | 2/1993 | Fabian et al. | 5,386,828 A | 2/1995 | Owens et al. |
| 5,190,059 A | 3/1993 | Fabian et al. | 5,389,101 A | 2/1995 | Heilbrun et al. |
| 5,193,106 A | 3/1993 | DeSena | 5,391,199 A | 2/1995 | Ben-Haim |
| 5,197,476 A | 3/1993 | Nowacki et al. | 5,394,457 A | 2/1995 | Leibinger et al. |
| 5,197,965 A | 3/1993 | Cherry et al. | 5,394,875 A | 3/1995 | Lewis et al. |
| 5,198,768 A | 3/1993 | Keren | 5,397,329 A | 3/1995 | Allen |
| 5,198,877 A | 3/1993 | Schulz | 5,398,684 A | 3/1995 | Hardy |
| 5,207,688 A | 5/1993 | Carol | 5,399,146 A | 3/1995 | Nowacki et al. |
| 5,211,164 A | 5/1993 | Allen | 5,400,384 A | 3/1995 | Fernandes et al. |
| 5,211,165 A | 5/1993 | Dumoulin et al. | 5,402,801 A | 4/1995 | Taylor |
| 5,211,176 A | 5/1993 | Ishiguro et al. | 5,408,409 A | 4/1995 | Glassman et al. |
| 5,212,720 A | 5/1993 | Landi et al. | 5,413,573 A | 5/1995 | Koivukangas |
| 5,214,615 A | 5/1993 | Bauer | 5,417,210 A | 5/1995 | Funda et al. |
| 5,217,003 A | 6/1993 | Wilk | 5,419,325 A | 5/1995 | Dumoulin et al. |
| 5,217,453 A | 6/1993 | Wilk | 5,423,334 A | 6/1995 | Jordan |
| 5,219,351 A | 6/1993 | Teubner et al. | 5,425,367 A | 6/1995 | Shapiro et al. |
| 5,222,499 A | 6/1993 | Allen et al. | 5,425,382 A | 6/1995 | Golden et al. |
| 5,224,049 A | 6/1993 | Mushabac | 5,426,683 A | 6/1995 | O'Farrell, Jr. et al. |
| 5,228,442 A | 7/1993 | Imran | 5,426,687 A | 6/1995 | Goodall et al. |
| 5,230,338 A | 7/1993 | Allen et al. | 5,427,097 A | 6/1995 | Depp |
| 5,230,623 A | 7/1993 | Guthrie et al. | 5,429,132 A | 7/1995 | Guy et al. |
| 5,233,990 A | 8/1993 | Barnea | 5,433,198 A | 7/1995 | Desai |
| 5,237,996 A | 8/1993 | Waldman et al. | RE35,025 E | 8/1995 | Anderton |
| 5,249,581 A | 10/1993 | Horbal et al. | 5,437,277 A | 8/1995 | Dumoulin et al. |
| 5,251,127 A | 10/1993 | Raab | 5,443,066 A | 8/1995 | Dumoulin et al. |
| 5,251,635 A | 10/1993 | Dumoulin et al. | 5,443,489 A | 8/1995 | Ben-Haim |
| 5,253,647 A | 10/1993 | Takahashi et al. | 5,444,756 A | 8/1995 | Pai et al. |
| 5,255,680 A | 10/1993 | Darrow et al. | 5,445,144 A | 8/1995 | Wodicka et al. |
| 5,257,636 A | 11/1993 | White | 5,445,150 A | 8/1995 | Dumoulin et al. |
| 5,257,998 A | 11/1993 | Ota et al. | 5,445,166 A | 8/1995 | Taylor |
| 5,261,404 A | 11/1993 | Mick et al. | 5,446,548 A | 8/1995 | Gerig et al. |
| 5,265,610 A | 11/1993 | Darrow et al. | 5,447,154 A | 9/1995 | Cinquin et al. |
| 5,265,611 A | 11/1993 | Hoenig et al. | 5,448,610 A | 9/1995 | Yamamoto et al. |
| 5,269,759 A | 12/1993 | Hernandez et al. | 5,453,686 A | 9/1995 | Anderson |
| 5,271,400 A | 12/1993 | Dumoulin et al. | 5,456,718 A | 10/1995 | Szymaitis |
| 5,273,025 A | 12/1993 | Sakiyama et al. | 5,457,641 A | 10/1995 | Zimmer et al. |
| 5,274,551 A | 12/1993 | Corby, Jr. | 5,458,718 A | 10/1995 | Venkitachalam |
| 5,279,309 A | 1/1994 | Taylor et al. | 5,464,446 A | 11/1995 | Dreessen et al. |
| 5,285,787 A | 2/1994 | Machida | 5,469,847 A | 11/1995 | Zinreich et al. |
| 5,291,199 A | 3/1994 | Overman et al. | 5,478,341 A | 12/1995 | Cook et al. |
| 5,291,889 A | 3/1994 | Kenet et al. | 5,478,343 A | 12/1995 | Ritter |
| 5,295,483 A | 3/1994 | Nowacki et al. | 5,480,422 A | 1/1996 | Ben-Haim |
| 5,297,549 A | 3/1994 | Beatty et al. | 5,480,439 A | 1/1996 | Bisek et al. |
| 5,299,253 A | 3/1994 | Wessels | 5,483,961 A | 1/1996 | Kelly et al. |
| 5,299,254 A | 3/1994 | Dancer et al. | 5,484,437 A | 1/1996 | Michelson |
| 5,299,288 A | 3/1994 | Glassman et al. | 5,485,849 A | 1/1996 | Panescu et al. |
| 5,300,080 A | 4/1994 | Clayman et al. | 5,487,391 A | 1/1996 | Panescu |
| 5,305,091 A | 4/1994 | Gelbart et al. | 5,487,729 A | 1/1996 | Avellanet et al. |
| 5,305,203 A | 4/1994 | Raab | 5,487,757 A | 1/1996 | Truckai et al. |
| 5,306,271 A | 4/1994 | Zinreich et al. | 5,490,196 A | 2/1996 | Rudich et al. |
| 5,307,072 A | 4/1994 | Jones, Jr. | 5,490,852 A * | 2/1996 | Azer et al. .................. 606/79 |
| 5,309,913 A | 5/1994 | Kormos et al. | 5,494,034 A | 2/1996 | Schlondorff et al. |
| 5,315,630 A | 5/1994 | Sturm et al. | 5,503,416 A | 4/1996 | Aoki et al. |
| 5,316,024 A | 5/1994 | Hirschi et al. | 5,513,637 A | 5/1996 | Twiss et al. |
| 5,318,025 A | 6/1994 | Dumoulin et al. | 5,514,146 A | 5/1996 | Lam et al. |
| 5,320,111 A | 6/1994 | Livingston | 5,515,160 A | 5/1996 | Schulz et al. |
| 5,325,728 A | 7/1994 | Zimmerman et al. | 5,517,990 A | 5/1996 | Kalfas et al. |
| 5,325,873 A | 7/1994 | Hirschi et al. | 5,531,227 A | 7/1996 | Schneider |
| 5,329,944 A | 7/1994 | Fabian et al. | 5,531,520 A | 7/1996 | Grimson et al. |

| | | | | | |
|---|---|---|---|---|---|
| 5,542,938 A | 8/1996 | Avellanet et al. | 5,749,362 A | 5/1998 | Funda et al. |
| 5,543,951 A | 8/1996 | Moehrmann | 5,749,835 A | 5/1998 | Glantz |
| 5,546,940 A | 8/1996 | Panescu et al. | 5,752,513 A | 5/1998 | Acker et al. |
| 5,546,949 A | 8/1996 | Frazin et al. | 5,755,725 A | 5/1998 | Druais |
| 5,546,951 A | 8/1996 | Ben-Haim | RE35,816 E | 6/1998 | Schulz |
| 5,551,429 A | 9/1996 | Fitzpatrick et al. | 5,758,667 A | 6/1998 | Slettenmark |
| 5,558,091 A | 9/1996 | Acker et al. | 5,762,064 A | 6/1998 | Polvani |
| 5,566,681 A | 10/1996 | Manwaring et al. | 5,767,669 A | 6/1998 | Hansen et al. |
| 5,568,384 A | 10/1996 | Robb et al. | 5,767,699 A | 6/1998 | Bosnyak et al. |
| 5,568,809 A | 10/1996 | Ben-haim | 5,767,960 A | 6/1998 | Orman |
| 5,571,109 A | 11/1996 | Bertagnoli | 5,769,789 A | 6/1998 | Wang et al. |
| 5,572,999 A | 11/1996 | Funda et al. | 5,769,843 A | 6/1998 | Abela et al. |
| 5,573,533 A | 11/1996 | Strul | 5,769,861 A | 6/1998 | Vilsmeier |
| 5,575,794 A | 11/1996 | Walus et al. | 5,772,594 A | 6/1998 | Barrick |
| 5,575,798 A | 11/1996 | Koutrouvelis | 5,772,661 A | 6/1998 | Michelson |
| 5,583,909 A | 12/1996 | Hanover | 5,775,322 A | 7/1998 | Silverstein et al. |
| 5,588,430 A | 12/1996 | Bova et al. | 5,776,064 A | 7/1998 | Kalfas et al. |
| 5,590,215 A | 12/1996 | Allen | 5,782,765 A | 7/1998 | Jonkman |
| 5,592,939 A | 1/1997 | Martinelli | 5,787,886 A | 8/1998 | Kelly et al. |
| 5,595,193 A | 1/1997 | Walus et al. | 5,788,701 A | 8/1998 | McCue |
| 5,596,228 A | 1/1997 | Anderton et al. | 5,792,055 A | 8/1998 | McKinnon |
| 5,600,330 A | 2/1997 | Blood | 5,795,294 A | 8/1998 | Luber et al. |
| 5,603,318 A | 2/1997 | Heilbrun et al. | 5,797,849 A | 8/1998 | Vesely et al. |
| 5,611,025 A | 3/1997 | Lorensen et al. | 5,799,055 A | 8/1998 | Peshkin et al. |
| 5,617,462 A | 4/1997 | Spratt | 5,799,099 A | 8/1998 | Wang et al. |
| 5,617,857 A | 4/1997 | Chader et al. | 5,800,352 A | 9/1998 | Ferre et al. |
| 5,619,261 A | 4/1997 | Anderton | 5,800,535 A | 9/1998 | Howard, III |
| 5,622,169 A | 4/1997 | Golden et al. | 5,802,719 A | 9/1998 | O'Farrell, Jr. et al. |
| 5,622,170 A | 4/1997 | Schulz | 5,803,089 A | 9/1998 | Ferre et al. |
| 5,627,873 A | 5/1997 | Hanover et al. | 5,807,252 A | 9/1998 | Hassfeld et al. |
| 5,628,315 A | 5/1997 | Vilsmeier et al. | 5,808,665 A | 9/1998 | Green |
| 5,630,431 A | 5/1997 | Taylor | 5,810,008 A | 9/1998 | Dekel et al. |
| 5,636,644 A | 6/1997 | Hart et al. | 5,810,728 A | 9/1998 | Kuhn |
| 5,638,819 A | 6/1997 | Manwaring et al. | 5,810,735 A | 9/1998 | Halperin et al. |
| 5,640,170 A | 6/1997 | Anderson | 5,820,553 A | 10/1998 | Hughes |
| 5,642,395 A | 6/1997 | Anderton et al. | 5,823,192 A | 10/1998 | Kalend et al. |
| 5,643,268 A | 7/1997 | Vilsmeier et al. | 5,823,958 A | 10/1998 | Truppe |
| 5,645,065 A | 7/1997 | Shapiro et al. | 5,828,725 A | 10/1998 | Levinson |
| 5,646,524 A | 7/1997 | Gilboa | 5,828,770 A | 10/1998 | Leis et al. |
| 5,647,361 A | 7/1997 | Damadian | 5,829,444 A | 11/1998 | Ferre et al. |
| 5,662,111 A | 9/1997 | Cosman | 5,831,260 A | 11/1998 | Hansen |
| 5,664,001 A | 9/1997 | Tachibana et al. | 5,833,608 A | 11/1998 | Acker |
| 5,674,296 A | 10/1997 | Bryan et al. | 5,834,759 A | 11/1998 | Glossop |
| 5,676,673 A | 10/1997 | Ferre et al. | 5,836,954 A | 11/1998 | Heilbrun et al. |
| 5,681,260 A | 10/1997 | Ueda et al. | 5,840,024 A | 11/1998 | Taniguchi et al. |
| 5,682,886 A | 11/1997 | Delp et al. | 5,840,025 A | 11/1998 | Ben-Haim |
| 5,682,890 A | 11/1997 | Kormos et al. | 5,843,076 A | 12/1998 | Webster, Jr. et al. |
| 5,690,108 A | 11/1997 | Chakeres | 5,848,967 A | 12/1998 | Cosman |
| 5,690,636 A | 11/1997 | Wildgoose et al. | 5,851,183 A | 12/1998 | Bucholz |
| 5,694,945 A | 12/1997 | Ben-Haim | 5,865,846 A | 2/1999 | Bryan et al. |
| 5,695,500 A | 12/1997 | Taylor et al. | 5,868,674 A | 2/1999 | Glowinski et al. |
| 5,695,501 A | 12/1997 | Carol et al. | 5,868,675 A | 2/1999 | Henrion et al. |
| 5,696,500 A | 12/1997 | Taylor et al. | 5,871,445 A | 2/1999 | Bucholz |
| 5,697,377 A | 12/1997 | Wittkampf | 5,871,455 A | 2/1999 | Ueno |
| 5,702,406 A | 12/1997 | Vilsmeier et al. | 5,871,487 A | 2/1999 | Warner et al. |
| 5,711,299 A | 1/1998 | Manwaring et al. | 5,873,822 A | 2/1999 | Ferre et al. |
| 5,713,946 A | 2/1998 | Ben-Haim | 5,882,304 A | 3/1999 | Ehnholm et al. |
| 5,715,822 A | 2/1998 | Watkins | 5,884,410 A | 3/1999 | Prinz |
| 5,715,836 A | 2/1998 | Kliegis et al. | 5,889,834 A | 3/1999 | Vilsmeier et al. |
| 5,718,241 A | 2/1998 | Ben-Haim et al. | 5,891,034 A | 4/1999 | Bucholz |
| 5,727,552 A | 3/1998 | Ryan | 5,891,157 A | 4/1999 | Day et al. |
| 5,727,553 A | 3/1998 | Saad | 5,904,691 A | 5/1999 | Barnett et al. |
| 5,729,129 A | 3/1998 | Acker | 5,907,395 A | 5/1999 | Schulz et al. |
| 5,730,129 A | 3/1998 | Darrow et al. | 5,913,820 A | 6/1999 | Bladen et al. |
| 5,730,130 A | 3/1998 | Fitzpatrick et al. | 5,916,164 A | 6/1999 | Fitzpatrick et al. |
| 5,732,703 A | 3/1998 | Kalfas et al. | 5,920,395 A | 7/1999 | Schulz |
| 5,735,278 A | 4/1998 | Hoult et al. | 5,921,992 A | 7/1999 | Costales et al. |
| 5,738,096 A | 4/1998 | Ben-Haim | 5,923,727 A | 7/1999 | Navab |
| 5,740,802 A | 4/1998 | Nafis et al. | 5,928,248 A | 7/1999 | Acker |
| 5,741,214 A | 4/1998 | Ouchi et al. | 5,938,603 A | 8/1999 | Ponzi |
| 5,742,394 A | 4/1998 | Hansen | 5,938,694 A | 8/1999 | Jaraczewski et al. |
| 5,744,953 A | 4/1998 | Hansen | 5,947,980 A | 9/1999 | Jensen et al. |
| 5,748,767 A | 5/1998 | Raab | 5,947,981 A | 9/1999 | Cosman |

| | | | | | | |
|---|---|---|---|---|---|---|
| 5,950,629 | A | 9/1999 | Taylor et al. | 6,437,567 B1 | 8/2002 | Schenck et al. |
| 5,951,475 | A | 9/1999 | Gueziec et al. | 6,445,943 B1 | 9/2002 | Ferre et al. |
| 5,951,571 | A | 9/1999 | Audette | 6,450,978 B1 * | 9/2002 | Brosseau et al. ............ 600/595 |
| 5,954,647 | A | 9/1999 | Bova et al. | 6,470,207 B1 | 10/2002 | Simon et al. |
| 5,957,844 | A | 9/1999 | Dekel et al. | 6,474,341 B1 | 11/2002 | Hunter et al. |
| 5,964,796 | A | 10/1999 | Imran | 6,478,802 B2 | 11/2002 | Kienzle, III et al. |
| 5,967,980 | A | 10/1999 | Ferre et al. | 6,484,049 B1 | 11/2002 | Seeley et al. |
| 5,967,982 | A | 10/1999 | Barnett | 6,490,467 B1 | 12/2002 | Bucholz et al. |
| 5,968,047 | A | 10/1999 | Reed | 6,490,475 B1 | 12/2002 | Seeley et al. |
| 5,971,997 | A | 10/1999 | Guthrie et al. | 6,493,573 B1 | 12/2002 | Martinelli et al. |
| 5,976,156 | A | 11/1999 | Taylor et al. | 6,498,944 B1 | 12/2002 | Ben-Haim et al. |
| 5,980,535 | A | 11/1999 | Barnett et al. | 6,499,488 B1 | 12/2002 | Hunter et al. |
| 5,983,126 | A | 11/1999 | Wittkampf | 6,516,046 B1 | 2/2003 | Fröhlich et al. |
| 5,987,349 | A | 11/1999 | Schulz | 6,527,443 B1 | 3/2003 | Vilsmeier et al. |
| 5,987,960 | A | 11/1999 | Messner et al. | 6,551,325 B2 | 4/2003 | Neubauer et al. |
| 5,999,837 | A | 12/1999 | Messner et al. | 6,575,899 B1 * | 6/2003 | Foley et al. ................. 600/114 |
| 5,999,840 | A | 12/1999 | Grimson et al. | 6,584,174 B2 | 6/2003 | Schubert et al. |
| 6,001,130 | A | 12/1999 | Bryan et al. | 6,609,022 B2 | 8/2003 | Vilsmeier et al. |
| 6,006,126 | A | 12/1999 | Cosman | 6,611,700 B1 | 8/2003 | Vilsmeier et al. |
| 6,006,127 | A | 12/1999 | Van Der Brug et al. | 6,640,128 B2 | 10/2003 | Vilsmeier et al. |
| 6,013,087 | A | 1/2000 | Adams et al. | 6,662,036 B2 | 12/2003 | Cosman |
| 6,014,580 | A | 1/2000 | Blume et al. | 6,694,162 B2 | 2/2004 | Hartlep |
| 6,016,439 | A | 1/2000 | Acker | 6,694,168 B2 | 2/2004 | Traxel et al. |
| 6,019,725 | A | 2/2000 | Vesely et al. | 6,701,179 B1 | 3/2004 | Martinelli et al. |
| 6,024,695 | A | 2/2000 | Greenberg et al. | 6,725,082 B2 | 4/2004 | Sati et al. |
| 6,033,406 | A * | 3/2000 | Mathews ................... 606/279 | 6,980,849 B2 | 12/2005 | Sasso |
| 6,050,724 | A | 4/2000 | Schmitz et al. | 6,993,374 B2 | 1/2006 | Sasso |
| 6,052,477 | A | 4/2000 | Wang et al. | 7,237,556 B2 * | 7/2007 | Smothers et al. ............ 128/898 |
| 6,059,718 | A | 5/2000 | Taniguchi et al. | 2001/0007918 A1 | 7/2001 | Vilsmeier et al. |
| 6,063,022 | A | 5/2000 | Ben-Haim | 2002/0038085 A1 | 3/2002 | Immerz |
| 6,071,288 | A | 6/2000 | Carol et al. | 2002/0095081 A1 | 7/2002 | Vilsmeier |
| 6,073,043 | A | 6/2000 | Schneider | 2002/0198451 A1 | 12/2002 | Carson |
| 6,076,008 | A | 6/2000 | Bucholz | 2003/0066538 A1 | 4/2003 | Martinelli et al. |
| 6,096,050 | A | 8/2000 | Audette | 2003/0153829 A1 | 8/2003 | Sarin et al. |
| 6,104,944 | A | 8/2000 | Martinelli | 2003/0196671 A1 | 10/2003 | Sasso |
| 6,118,845 | A | 9/2000 | Simon et al. | 2003/0225329 A1 | 12/2003 | Rossner et al. |
| 6,122,538 | A | 9/2000 | Sliwa, Jr. et al. | 2004/0024309 A1 | 2/2004 | Ferre et al. |
| 6,122,541 | A | 9/2000 | Cosman et al. | 2004/0030236 A1* | 2/2004 | Mazzocchi et al. .......... 600/414 |
| 6,131,396 | A | 10/2000 | Duerr et al. | 2004/0030237 A1 | 2/2004 | Lee et al. |
| 6,139,183 | A | 10/2000 | Graumann | 2004/0068263 A1 | 4/2004 | Chouinard et al. |
| 6,147,480 | A | 11/2000 | Osadchy et al. | 2004/0097952 A1 | 5/2004 | Sarin et al. |
| 6,149,592 | A | 11/2000 | Yanof et al. | 2004/0106926 A1 | 6/2004 | Leitner et al. |
| 6,156,067 | A | 12/2000 | Bryan et al. | 2004/0167393 A1 | 8/2004 | Solar et al. |
| 6,161,032 | A | 12/2000 | Acker | 2004/0171924 A1* | 9/2004 | Mire et al. ................... 600/407 |
| 6,165,181 | A | 12/2000 | Heilbrun et al. | 2004/0230199 A1 | 11/2004 | Jansen et al. |
| 6,167,296 | A | 12/2000 | Shahidi | 2004/0267242 A1 | 12/2004 | Grimm et al. |
| 6,172,499 | B1 | 1/2001 | Ashe | 2005/0085720 A1* | 4/2005 | Jascob et al. ................. 600/424 |
| 6,175,756 | B1 | 1/2001 | Ferre et al. | 2006/0253152 A1* | 11/2006 | Evans et al. ................. 606/232 |
| 6,178,345 | B1 | 1/2001 | Vilsmeier et al. | | | |
| 6,194,639 | B1 | 2/2001 | Botella et al. | FOREIGN PATENT DOCUMENTS | | |
| 6,201,387 | B1 | 3/2001 | Govari | DE | 3042343 A1 | 6/1982 |
| 6,201,984 | B1 | 3/2001 | Funda et al. | DE | 35 08730 | 3/1985 |
| 6,203,497 | B1 | 3/2001 | Dekel et al. | DE | 37 17 871 | 5/1987 |
| 6,211,666 | B1 | 4/2001 | Acker | DE | 38 38011 | 11/1988 |
| 6,223,067 | B1 | 4/2001 | Vilsmeier | DE | 3831278 A1 | 3/1989 |
| 6,226,548 | B1 * | 5/2001 | Foley et al. ................. 600/426 | DE | 42 13 426 | 4/1992 |
| 6,233,476 | B1 | 5/2001 | Strommer et al. | DE | 42 25 112 | 7/1992 |
| 6,246,231 | B1 | 6/2001 | Ashe | DE | 4233978 C1 | 4/1994 |
| 6,259,942 | B1 | 7/2001 | Westermann et al. | DE | 197 15 202 | 4/1997 |
| 6,273,896 | B1 | 8/2001 | Franck et al. | DE | 197 47 427 | 10/1997 |
| 6,285,902 | B1 | 9/2001 | Kienzle, III et al. | DE | 197 51 761 | 11/1997 |
| 6,298,262 | B1 | 10/2001 | Franck et al. | DE | 198 32 296 | 7/1998 |
| 6,314,310 | B1 | 11/2001 | Ben-Haim et al. | DE | 10085137 | 11/2002 |
| 6,332,089 | B1 | 12/2001 | Acker et al. | EP | 0 062 941 | 3/1982 |
| 6,341,231 | B1 | 1/2002 | Ferre et al. | EP | 0 119 660 | 9/1984 |
| 6,348,058 | B1 * | 2/2002 | Melkent et al. ............. 606/130 | EP | 0 155 857 | 1/1985 |
| 6,351,659 | B1 | 2/2002 | Vilsmeier | EP | 0319844 A1 | 1/1988 |
| 6,381,485 | B1 | 4/2002 | Hunter et al. | EP | 0 326 768 | 12/1988 |
| 6,424,856 | B1 | 7/2002 | Vilsmeier et al. | EP | 0419729 A1 | 9/1989 |
| 6,427,314 | B1 | 8/2002 | Acker | EP | 0350996 A1 | 1/1990 |
| 6,428,547 | B1 | 8/2002 | Vilsmeier et al. | EP | 0651968 A1 | 8/1990 |
| 6,430,434 | B1 | 8/2002 | Mittelstadt | EP | 0 427 358 | 10/1990 |
| 6,434,415 | B1 | 8/2002 | Foley et al. | | | |

| | | |
|---|---|---|
| EP | 0 456 103 | 5/1991 |
| EP | 0581704 B1 | 7/1993 |
| EP | 0655138 B1 | 8/1993 |
| EP | 0894473 A2 | 1/1995 |
| EP | 0469966 | 8/1995 |
| EP | 0 930 046 | 10/1998 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 11/1989 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 95/07055 | 9/1994 |
| WO | WO 94/23647 | 10/1994 |
| WO | WO 94/24933 | 11/1994 |
| WO | WO 96/32059 | 11/1995 |
| WO | WO 96/11624 | 4/1996 |
| WO | WO 97/49453 | 6/1997 |
| WO | WO 97/36192 | 10/1997 |
| WO | WO 99/23956 | 11/1997 |
| WO | WO 98/08554 | 3/1998 |
| WO | WO 98/38908 | 9/1998 |
| WO | WO 99/15097 | 9/1998 |
| WO | WO 99/21498 | 10/1998 |
| WO | WO 99/27839 | 12/1998 |
| WO | WO 99/33406 | 12/1998 |
| WO | WO 99/38449 | 1/1999 |
| WO | WO 99/52094 | 4/1999 |
| WO | WO 99/26549 | 6/1999 |
| WO | WO 99/29253 | 6/1999 |
| WO | WO 99/37208 | 7/1999 |
| WO | WO 99/60939 | 12/1999 |
| WO | WO 01/30437 A1 | 5/2001 |

OTHER PUBLICATIONS

Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 4, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.

Brown, R., M.D., A Stereotactic Head Frame for Use with CT Body Scanners, Investigative Radiology © J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N. A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE —The Intl. Soc. For Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May, 1992.
Champleboux, "Utilisation de Fonctions Splines pour la Mise au Point D'un Capteur Tridimensionnel sans Contact," Quelques Applications Medicates, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (undated.
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.

Gottesfeld Brown et al., "Registration of Planar Film Radiographs with Computer Tomography," Proceedings of MMBIA, Jun. 1996, pp. 42-51.

Grimson, W.E.L., An Automatic Registration Method for Frameless Stereotaxy, Image Guided Surgery, and enhanced Reality Visualization, IEEE, pp. 430-436 (1994).

Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic-Interactive Cranial Surgery: The Operating Arm System, Handbook of Stereotaxy Using the CRW Apparatus, Chapter 13, pp. 193-211 (undated.

Hamadeh et al, "Kinematic Study of Lumbar Spine Using Functional Radiographies and 3D/2D Registration," TIMC UMR 5525—IMAG.

Hamadeh et al., "Automated 3-Dimensional Computed Tomographic and Fluorscopic Image Registration," Computer Aided Surgery (1998), 3:11-19.

Hamadeh et al., "Towards Automatic Registration Between CT and X-ray Images: Cooperation Between 3D/2D Registration and 2D Edge Detection," MRCAS '95, pp. 39-46.

Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).

Hatch, "Reference-Display System for the Integration of CT Scanning and the Operating Microscope," Thesis, Thayer School of Engineering, Oct. 1984, pp. 1-189.

Hatch, et al., "Reference-Display System for the Integration of CT Scanning and the Operating Microscope", Proceedings of the Eleventh Annual Northeast Bioengineering Conference, Mar. 14-15, 1985, pp. 252-254.

Heilbrun et al., "Preliminary experience with Brown-Roberts-Wells (BRW) computerized tomography stereotaxic guidance system," Journal of Neurosurgery, vol. 59, Aug. 1983, pp. 217-222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).

Heilbrun, M.P., Computed Tomography—Guided Stereotactic Systems, Clinical Neurosurgery, Chapter 31, pp. 564-581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).

Henderson et al., "An Accurate and Ergonomic Method of Registration for Image-guided Neurosurgery," Computerized Medical Imaging and Graphics, vol. 18, No. 4, Jul.-Aug. 1994, pp. 273-277.

Hoerenz, "The Operating Microscope I. Optical Principles, Illumination Systems, and Support Systems," Journal of Microsurgery, vol. 1, 1980, pp. 364-369.

Hofstetter et al., "Fluoroscopy Based Surgical Navigation—Concept and Clinical Applications," Computer Assisted Radiology and Surgery, 1997, pp. 956-960.

Horner et al., "A Comparison of CT-Stereotaxic Brain Biopsy Techniques," Investigative Radiology, Sep.-Oct. 1984, pp. 367-373.

Hounsfield, "Computerized transverse axial scanning (tomography): Part 1. Description of system," British Journal of Radiology, vol. 46, No. 552, Dec. 1973, pp. 1016-1022.

Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.

Jacques et al., "Computerized three-dimensional stereotaxic removal of small central nervous system lesion in patients," J. Neurosurg., vol. 53, Dec. 1980, pp. 816-820.

Joskowicz et al., "Computer-Aided Image-Guided Bone Fracture Surgery: Concept and Implementation," CAR '98, pp. 710-715.

Kall, B., The Impact of Computer and Imgaging Technology on Stereotactic Surgery, Proceedings of the Meeting of the American Society for Stereotactic and Functional Neurosurgery, pp. 10-22 (1987).

Kato, A., et al., A frameless, armless navigational system for computer-assisted neurosurgery, J. Neurosurg., vol. 74, pp. 845-849 (May 1991).

Kelly et al., "Computer-assisted stereotaxic laser resection of intra-axial brain neoplasms," Journal of Neurosurgery, vol. 64, Mar. 1986, pp. 427-439.

Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).

Kelly, P.J., Computer-Directed Stereotactic Resection of Brain Tumors, Neurologica Operative Atlas, vol. 1, No. 4, pp. 299-313 (1991).

Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).

Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).

Kim, W.S. et al., A Helmet Mounted Display for Telerobotics, IEEE, pp. 543-547 (1988).

Klimek, L., et al., Long-Term Experience with Different Types of Localization Systems in Skull-Base Surgery, Ear, Nose & Throat Surgery, Chapter 51, pp. 635-638 (undated).

Kosugi, Y., et al., An Articulated Neurosurgical Navigation System Using MRI and CT Images, IEEE Trans. on Biomed, Eng. vol. 35, No. 2, pp. 147-152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).

Kwoh, Y.S., Ph.D., et al., A New Computerized Tomographic-Aided Robotic Stereotaxis System, Robotics Age, vol. 7, No. 6, pp. 17-22 (Jun. 1985).

Laitinen et al., "An Adapter for Computed Tomography-Guided, Stereotaxis," Surg. Neurol., 1985, pp. 559-566.

Laitinen, "Noninvasive multipurpose stereoadapter," Neurological Research, Jun. 1987, pp. 137-141.

Lavallee et al, "Matching 3-D Smooth Surfaces with their 2-D Projections using 3-D Distance Maps," SPIE, vol. 1570, Geometric Methods in Computer Vision, 1991, pp. 322-336.

Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.

Lavallee et al., "Computer Assisted Spine Surgery: A Technique For Accurate Transpedicular Screw Fixation Using CT Data and a 3-D Optical Localizer," TIMC, Faculte de Medecine de Grenoble.

Lavallee et al., "Image guided operating robot: a clinical application in stereotactic neurosurgery," . Proceedings of the 1992 IEEE Internation Conference on Robotics and Automation, May 1992, pp. 618-624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926-0927.

Lavallee "VI Adaption de la Methodologie a Quelques Applications Cliniques," Chapitre VI, pp. 133-148.

Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).

Lavallee, S., et al., Computer Assisted Medical Interventions, NATO ASI Series, vol. F 60, 3d Imaging in Medic., pp. 301-312 (1990).

Leavitt, D.D., et al., Dynamic Field Shaping to Optimize Stereotactic Radiosurgery, I.J. Rad. Onc. Biol. Physc., vol. 21, pp. 1247-1255 (1991).

Leksell et al., "Stereotaxis and Tomography—A Technical Note," ACTA Neurochirurgica, vol. 52, 1980, pp. 1-7.

Lemieux et al., "A Patient-to-Computed-Tomography Image Registration Method Based on Digitally Reconstructed Radiographs," Med. Phys. 21 (11), Nov. 1994, pp. 1749-1760.

Levin et al., "The Brain: Integrated Three-dimensional Display of MR and PET Images," Radiology, vol. 172, No. 3, Sep. 1989, pp. 783-789.

Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).

Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.

McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).

Merloz, et al., "Computer Assisted Spine Surgery", Clinical Assisted Spine Surgery, No. 337, pp. 86-96.

Ng, W.S. et al., Robotic Surgery—A First-Hand Experience in Transurethral Resection of the Prostate Surgery, IEEE Eng. in Med. and Biology, pp. 120-125 (Mar. 1993).

Pelizzari et al., "Accurate Three-Dimensional Registration of CT, PET, and/or MR Images of the Brain," Journal of Computer Assisted Tomography, Jan./Feb. 1989, pp. 20-26.

Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).

Pelizzari et al., No. 52813 "Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157-163 (Sep.-Oct. 1978).

Phillips et al., "Image Guided Orthopaedic Surgery Design and Analysis," Trans Inst. MC, vol. 17, No. 5, 1995, pp. 251-264.

Pixsys, 3-D Digitizing Accessories, by Pixsys (marketing brochure)(undated) (2 pages).

Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.

Prestige Cervical Disc System Surgical Technique, 12 pgs.

Reinhardt et al., "CT-Guided 'Real Time' Stereotaxy," ACTA Neurochirurgica, 1989.

Reinhardt, H., et al., A Computer-Assisted Device for Intraoperative CT-Correlated Localization of Brain Tumors, pp. 51-58 (1988).

Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).

Reinhardt, H.F., et al., Mikrochirugische Enfferung tiefliegender Gefäβmiβbildungen mit Hilfe der Sonar-Stereometrie (Microsurgical Removal of Deep-Seated Vascular Malformations Using Sonar Stereometry). Ultraschall in Med. 12, pp. 80-83 (1991).

Reinhardt, Hans. F., Neuronavigation: A Ten-Year Review, Neurosurgery, pp. 329-341 (undated).

Roberts et al., "A frameless stereotaxic integration of computerized tomographic imaging and the operating microscope," J. Neurosurg., vol. 65, Oct. 1986, pp. 545-549.

Rosenbaum et al., "Computerized Tomography Guided Stereotaxis: A New Approach," Applied Neurophysiology, vol. 43, No. 3-5, 1980, pp. 172-173.

Sautot, "Vissage Pediculaire Assiste Par Ordinateur," Sep. 20, 1994.

Schueler et al., "Correction of Image Intensifier Distortion for Three-Dimensional X-Ray Angiography," SPIE Medical Imaging 1995, vol. 2432, pp. 272-279.

Selvik et al., "A Roentgen Stereophotogrammetric System," Acta Radiologica Diagnosis, 1983, pp. 343-352.

Shelden et al., "Development of a computerized microsteroetaxic method for localization and removal of minute CNS lesions under direct 3-D vision," J. Neurosurg., vol. 52, 1980, pp. 21-27.

Simon, D.A., Accuracy Validation in Image-Guided Orthopaedic Surgery, Second Annual Intl. Symp. on Med. Rob. an Comp-Assisted surgery, MRCAS '95, pp. 185-192 (undated).

Smith et al., "Computer Methods for Improved Diagnostic Image Display Applied to Stereotactic Neurosurgery," Automedical, vol. 14, 1992, pp. 371-382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient-image registration, J Neurosurgy, vol. 79, pp. 296-303 (Aug. 1993).

The Laitinen Stereotactic System, E2-E6.

Thompson, et al., A System for Anatomical and Functional Mapping of the Human Thalamus, Computers and Biomedical Research, vol. 10, pp. 9-24 (1977).

Trobraugh, J.W., et al., Frameless Stereotactic Ultrasonography: Method and Applications, Computerized Medical Imaging and Graphics, vol. 18, No. 4, pp. 235-246 (1994).

Viant et al., "A Computer Assisted Orthopaedic System for Distal Locking of Intramedullary Nails," Proc. of MediMEC '95, Bristol, 1995, pp. 86-91.

Von Hanwhr et al., Foreword, Computerized Medical Imaging and Graphics, vol. 18, No. 4, pp. 225-228, (Jul.-Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).

Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.

Watanabe, "Neuronavigator," lgaku-no-Ayumi, vol. 137, No. 6, May 10, 1986, pp. 1-4.

Watanabe, E., M.D., et al., Open Surgery Assisted by the Neuronavigator, a Stereotactic, Articulated, Sensitive Arm, Neurosurgery, vol. 28, No. 6, pp. 792-800 (1991).

Weese et al., "An Approach to 2D/3D Registration of a Vertebra in 2D X-ray Fluoroscopies with 3D CT Images," pp. 119-128.

International Search Report and Written Opinion mailed Mar. 20, 2007 for PCT/US06/36647 claiming benefit of U.S. Appl. No. 11/232,445, filed Sep. 21, 2005.

* cited by examiner

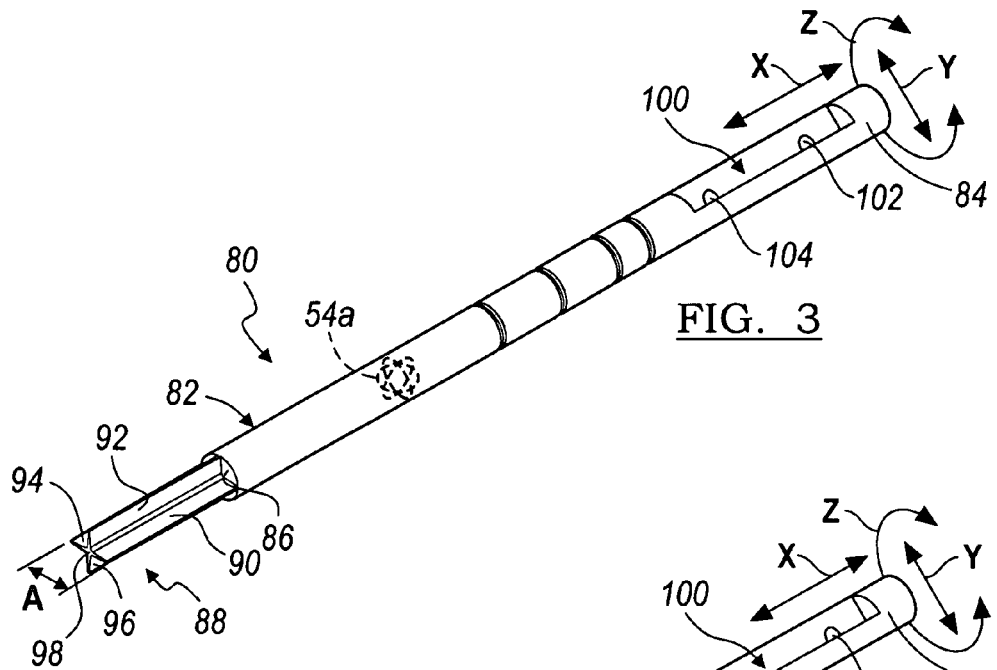
FIG. 3
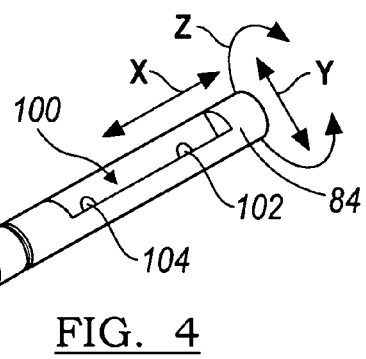
FIG. 4
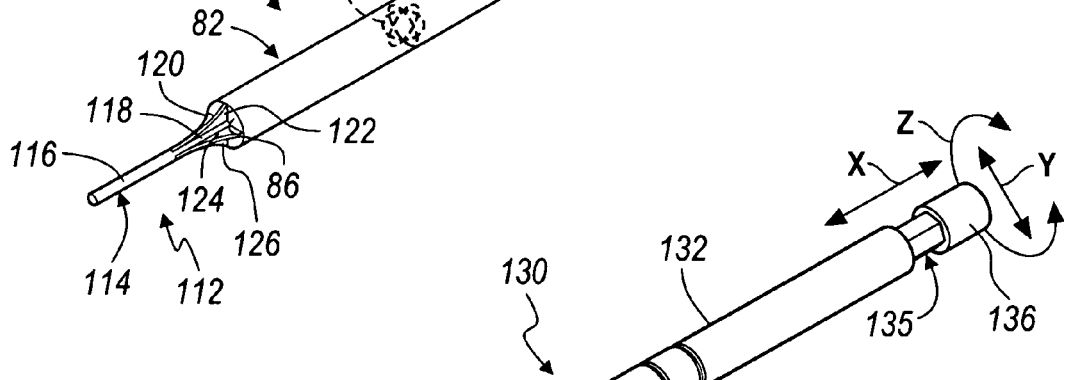
FIG. 5
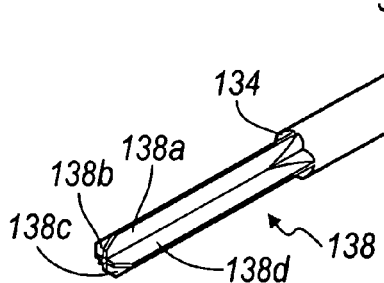

METHOD AND APPARATUS FOR POSITIONING A REFERENCE FRAME

FIELD

The present disclosure relates generally to navigated surgery, and more specifically, to a method and apparatus for performing a surgical procedure to repair, localize, and/or replace a selected portion of an anatomy.

BACKGROUND

Image guided medical and surgical procedures utilize patient images obtained prior to or during a medical procedure to guide a physician performing the procedure. Such procedures can be referred to as computer assisted procedures. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require a dynamic reference frame to track the position of the patient should patient movement occur during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure.

Various instruments that are desired to be tracked may be used during an operative procedure. Image data is generally acquired, either intra-operatively or pre-operatively, and the instrument is generally illustrated, and superimposed on the captured image data to identify the position of the instrument relative to the patient space. Therefore, the instrument may include tracking sensors, such as electromagnetic coils or optical detection points, such as LEDs or reflectors that may be detected by a suitable tracking system. Also, a dynamic reference frame (DRF) can be used by the tracking system to maintain a registration or localization of the patient space to the image space. The DRF can be also any appropriate tracking sensor that is fixed to a portion of the patient that allows the system to determine whether the patient has moved relative to the image space.

Other types of navigation systems operate as an image-less system, where an image of the body is not captured by an imaging device prior to the medical procedure, such as the device disclosed in U.S. patent application Ser. No. 10/687,539, entitled Method And Apparatus For Surgical Navigation Of A Multiple Piece Construct For Implantation, filed Oct. 16, 2003, incorporated herein by reference. With this type of procedure, the system may use a probe to contact certain landmarks in the body, such as landmarks on bone, where the system generates either a two-dimensional or three-dimensional model of the area of interest based upon these contacts. This way, when the surgical instrument or other object is tracked relative to this area, they can be superimposed on this model.

Generally, regardless of the whether the system is using images or imageless, a dynamic reference frame is used to maintain registration of the patient space with the navigated or image space. The position of the patient can be determined in real time relative to the images, implant, instruments, etc. with the use of a dynamic reference frame.

Most types of orthopedic medical procedures are performed using conventional surgical techniques, such as spine, hip, knee, shoulder, a synovial joint, and a facet joint. These techniques generally involve opening the patient in a manner to provide adequate viewing by the surgeon during the medical procedure. Use of the navigated procedure may enable more precise and accurate placement of an implant within the patient and may also enable surgery with diminished visualization.

Although a dynamic reference frame can be attached to an external or skin portion of a patient, it may be desirable to attach the dynamic reference frame to a bone portion. Nevertheless, it is desirable to allow the dynamic reference frame to be easily yet fixedly attached to the patient. It may also be desirable to fix the dynamic reference frame to the patient with a single member in an easy or simple procedure.

SUMMARY

According to various embodiments, a surgical navigation system to allow a processor assisted surgical procedure on an anatomy including a bone is disclosed. The system can include a tracking system operable to track a tracking sensor. A dynamic reference frame can include a tracking sensor to be tracked by the tracking system. Also, a dynamic reference frame positioning member can engage the bone in the anatomy to selectively fix the dynamic reference frame relative to the anatomy. The dynamic reference frame positioning member can be driven into the bone to hold the dynamic reference frame in a selected position.

According to various embodiments a dynamic reference frame positioning member can position a dynamic reference frame in a selected position relative to a bone. The positioning member can include a member extending between a first end and a second end. The member can define a dynamic reference frame engaging portion defined nearer the first end than the second end. Also a bone engaging portion can extend from near the second end. The bone engaging portion can include a first member and a second member extending at an angle relative to one another. Also, the bone engaging portion can be driven into the bone.

According to various embodiments a method of using a dynamic reference frame positioning member to position a dynamic reference frame relative to a selected portion of an anatomy including a bone is disclosed. The method can includes positioning a cannula through a soft tissue portion of the anatomy relative to the bone portion. A dynamic reference frame positioning member can be positioned through the positioned cannula and positioned into engagement with the bone. The dynamic reference frame positioning member can be fixed relative to the bone in at least one of a rotational motion, axial motion, translation motion, or combination thereof. Also, the cannula can be removed.

BRIEF DESCRIPTION OF THE DRAWINGS

The present teachings will become more fully understood from the detailed description and the accompanying drawings, wherein:

FIG. 3 is a positioning member according to various embodiments;

FIG. 4 is a positioning member according to various embodiments;

FIG. 5 is a positioning member according to various embodiments;

DETAILED DESCRIPTION OF VARIOUS EMBODIMENTS

The following description of various embodiments is merely exemplary in nature and is in no way intended to limit the teachings, its application, or uses. A method and apparatus to perform a procedure that can include a processor assisted surgical procedure. During the procedure, patient space and image space can be registered to allow for tracking of various tracking sensors. A dynamic reference frame can be selectively interconnected with a portion of the anatomy to maintain localization of the patient space with the image space. Although the following description describes the use of a dynamic reference frame positioning member in relation to a pelvis, it will be understood that the dynamic reference frame may be positioned in any portion of the anatomy. Further, the dynamic reference frame can be used for an orthopedic procedure, a spinal procedure, a cardiac procedure or any other surgical or medical procedure.

Figure 1:
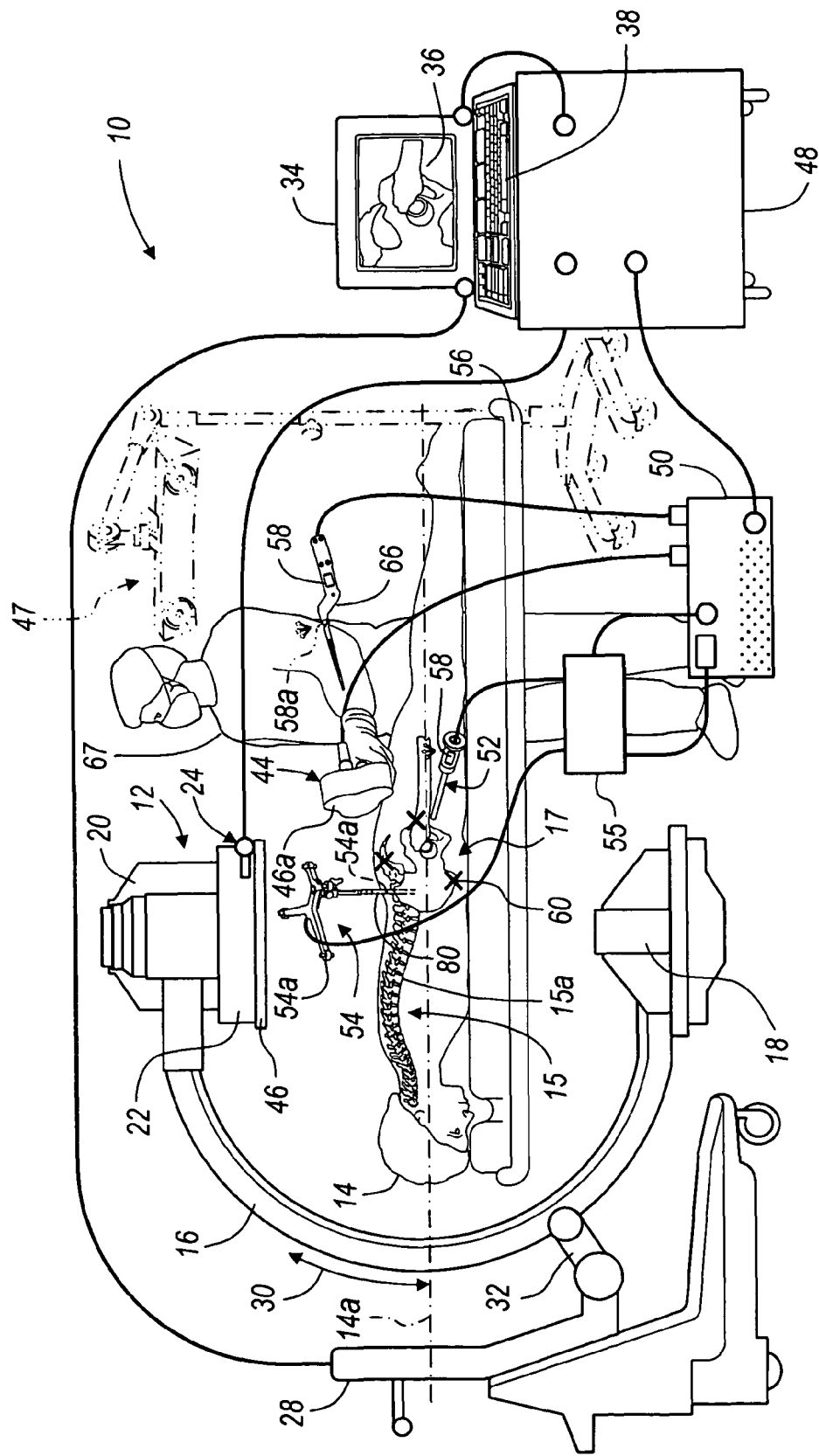
FIG. 1 is a diagram of a navigation system according to various teachings.

FIG. 1 is a diagram illustrating an overview of an image-guided navigation system 10 that can be used for various procedures. The navigation system 10 can be used to track the location of an implant, such as a spinal implant or orthopedic implant, relative to a patient 14. Also the navigation system 10 can track the position and orientation of various instruments. It should further be noted that the navigation system 10 may be used to navigate any type of instrument, implant, or delivery system, including: guide wires, arthroscopic systems, orthopedic implants, spinal implants, etc. Moreover, these instruments may be used to navigate or map any region of the body. The navigation system 10 and the various instruments may be used in any appropriate procedure, such as one that is generally minimally invasive or an open procedure.

The navigation system 10 may include an optional imaging device 12 that is used to acquire pre-, intra-, or post-operative or real-time image data of a patient 14. Alternatively various imageless systems can be used or images from atlas models can be used to produce patient images, such as those disclosed in U.S. patent application Ser. No. 10/687,539, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The optional imaging device 12 is, for example, a fluoroscopic x-ray imaging device that may be configured as a C-arm 16 having an x-ray source 18, an x-ray receiving section 20, an optional calibration and tracking target 22 and optional radiation sensors 24.

Image data may also be acquired using other imaging devices, such as those discussed above and herein. The calibration and tracking target 22 includes calibration markers 26 (see FIGS. 2A-2B), further discussed herein. An optional imaging device controller 28, that may control the C-arm 16, can capture the x-ray images received at the receiving section 20 and store the images for later use. The controller 28 may also be separate from the C-arm 16 and/or control the rotation of the C-arm 16. For example, the C-arm 16 can move in the direction of arrow 30 or rotate about a longitudinal axis 14a of the patient 14, allowing anterior or lateral views of the patient 14 to be imaged. Each of these movements involves rotation about a mechanical axis 32 of the C-arm 16.

In the example of FIG. 1, the longitudinal axis 14a of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the optional imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the imaging device 12 generates x-rays from the x-ray source 18 that propagate through the patient 14 and calibration and/or tracking target 22, into the x-ray receiving section 20. It will be understood that the tracking target need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data. Receiving section 20 may also be a digital device that converts x-rays directly to digital image data for forming images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for various procedures. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking.

The image data is then forwarded from the C-arm controller 28 to a navigation computer and/or processor controller or work station 34 having a display 36 and a user interface 38. It will also be understood that the image data is not necessarily first retained in the controller 28, but may also be directly transmitted to the navigation computer 34. The work station 34 provides facilities for displaying the image data as an image on the display 36, saving, digitally manipulating, or printing a hard copy image of the of the received image data. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 2B:
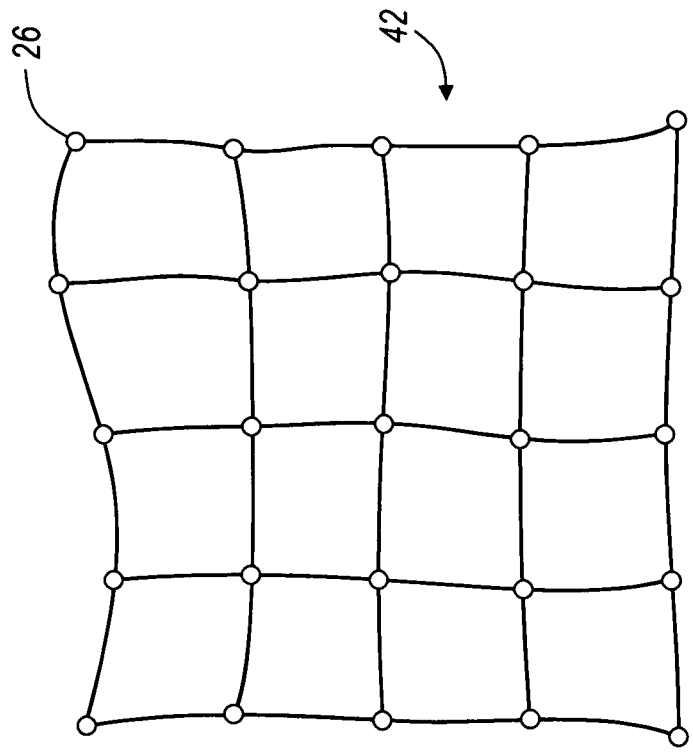
FIGS. 2A and 2B are diagrams representing undistorted and distorted views from a fluoroscopic imaging device.
Figure 2A:
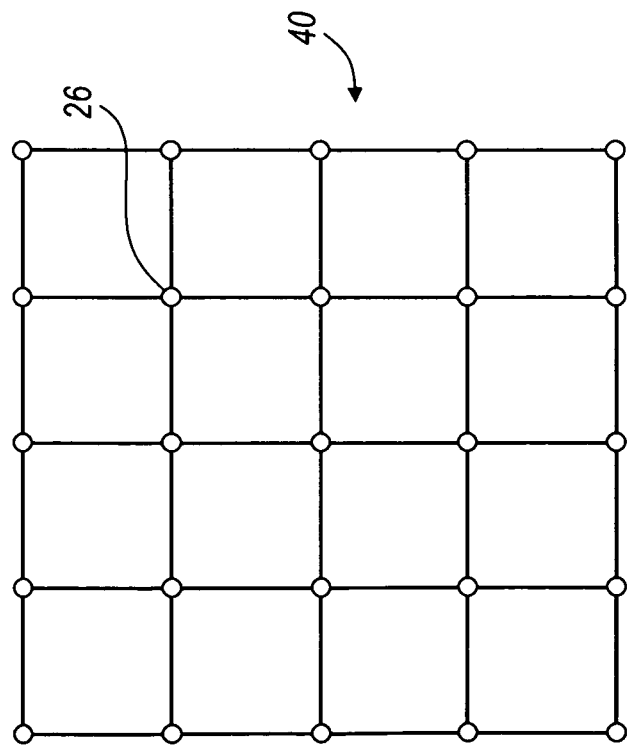

The optional imaging device 12, such as the fluoroscopic C-arm 16, that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 2A and 2B, respectively. The checkerboard shape, shown in FIG. 2A, represents the ideal image 40 of the checkerboard arranged calibration markers 26. The image taken by the receiving section 20, however, can suffer from distortion, as illustrated by the distorted calibration marker image 42, shown in FIG. 2B.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 2A). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intravascular ultrasound (IVUS), ultrasound, intra-operative CT or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 1, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, introduced and advanced in the patient 14, may be superimposed in more than one view on display 36 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction using dynamic reference frames.

Ultrasound imaging is also generally intra-operative procedure using a non-ionizing field to provide 2D, 3D, or 4D imaging, including anatomy and blood flow information. Ultrasound imaging provides automatic registration and does not need to account for any motion correction.

With continuing reference to FIG. 1, the navigation system 10 can further include an electromagnetic navigation or tracking system 44 that includes a localizer, such as a transmitter coil array 46, the coil array controller 48, a navigation probe interface 50, an instrument 52 and a dynamic reference frame 54. The dynamic reference frame 54 can be interconnected with a removable tracking sensor 54a or can include a more integral tracking sensor 54aa and a dynamic reference frame positioning member 80, according to various embodiments. It will be understood that reference to either the tracking sensor 54a or the integral tracking sensor 54aa can be a reference to either, unless specifically taught otherwise. Generally, the tracking sensor 54aa is tracked by the navigation system and the dynamic reference frame positioning member 80 fixes, as discussed further herein, the tracking sensor 54aa relative to the patient 14.

The instrument 52 may be any appropriate instrument, such as an instrument for preparing a portion of the patient or positioning an implant. The transmitter coil array 46 may also be supplemented or replaced with a mobile localizer 46a. The mobile localizer 46a may be one such as that described in U.S. patent application Ser. No. 10/941,782, filed Sep. 15, 2004, and entitled "METHOD AND APPARATUS FOR SURGICAL NAVIGATION", herein incorporated by reference. It will be understood that the tracking system may be any appropriate tracking system, such as an optical localizer illustrated in phantom at 47 such as the StealthStation® TRIA™ sold by Medtronic Navigation of Louisville, Colo. Other localization systems include an acoustic, radiation etc.

Further included in the navigation system 10 may be an isolator circuit or box 55. The isolator circuit or box 55 may be included in a transmission line to interrupt a line carrying a signal or a voltage to the navigation probe interface 50. Alternatively, the isolator circuit included in the isolator box 55 may be included in the navigation probe interface 50, the instrument 52, the dynamic reference frame 54, the transmission lines coupling the devices, or any other appropriate location. The isolator box 55 is operable to isolate any of the instruments or patient coincidence instruments or portions that are in contact with the patient should an undesirable electrical surge or voltage take place.

It should further be noted that the entire tracking system 44 or parts of the tracking system 44 may be incorporated into the imaging device 12, including the work station 34 and radiation sensors 24. Incorporating the tracking system 44 may provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 may also be positioned in the items being navigated, further discussed herein. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in a sensor 58 positioned on or in the instrument 52. These induced signals from the instrument 52 are delivered to the navigation probe interface 50 through the isolation circuit 55 and subsequently forwarded to the coil array controller 48. The navigation probe interface 50 may provide all the necessary electrical isolation for the navigation system 10. Alternatively, the electrical isolation may also be provided in the isolator box 55. Nevertheless, the isolator assembly 55 may be included in the navigation probe interface 50 or may be integrated into the instrument 52, and any other appropriate location. The navigation probe interface 50 can also include amplifiers, filters and buffers to directly interface with the sensors 58 in the instrument 52. Alternatively, the instrument 52 may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the instrument 52, the dynamic reference frame (DRF) 54, the probe 66, and others as will be described in detail below, are equipped with at least one, and generally multiple, tracking sensors 58, that may also be referred to as localization sensors. The instrument 52 can be a handle or inserter that interconnects with an attachment and may assist in placing an implant or in driving a portion. The instrument 52 can include a graspable or manipulable portion at a proximal end and the tracking sensor 58 may be fixed near the manipulable portion of the instrument 52. The tracking sensor 58 may be any appropriate tracking sensor 58 such as an optical sensor, acoustic sensor, or an electromagnetic sensor. If the sensor 58 includes an electromagnetic sensor the electromagnetic field generated by the transmitter coil array 46 may induce a current in the electromagnetic sensor 58. An alternative sensor may include an optical sensor, such as the optical sensor 58a, and may be used in addition to or in place of the electromagnetic sensor 58. The optical sensor may work with the optional optical array 47.

In an alternate embodiment, the electromagnetic sources or generators may be located within the instrument 52, DRF 54 (such as the integral tacking sensor 54aa), probe 66 and one or more receiver coils may be provided externally to the patient 14 forming a receiver coil array similar to the transmitter coil array 46. In this regard, the tracking sensors 58 could generate electromagnetic fields that would be received by the receiving coils in the receiving coil array similar to the transmitter coil array 46. Other types of tracking systems include optical, acoustic, electrical field, RF and accelerometers. Accelerometers enable both dynamic sensing due to motion and static sensing due to gravity. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The dynamic reference frame 54 of the tracking system 44 is also coupled to the navigation probe interface 50 to forward the information to the coil array controller 48. The dynamic reference frame 54, according to various embodiments, may include a small magnetic field detector. The dynamic reference frame 54 may be fixed to the patient 14 adjacent to the region being navigated so that any movement of the patient 14 is detected as relative motion between the transmitter coil array 46 and the dynamic reference frame 54. The dynamic reference frame 54 can be interconnected with the patient in any appropriate manner, including those discussed herein. This relative motion is forwarded to the coil array controller 48, which updates registration correlation and maintains accurate navigation, further discussed herein. The dynamic reference frame 54 may be any appropriate tracking sensor used as the dynamic reference frame 54 in the navigation system 10. Therefore the dynamic reference frame 54 may also be optical, acoustic, etc. If the dynamic reference frame 54 is electromagnetic it can be configured as a pair of orthogonally oriented coils, each having the same center or may be configured in any other non-coaxial or co-axial coil configurations.

The dynamic reference frame 54 may be affixed externally to the patient 14, adjacent to the region of navigation, such as on the patient's chest or pelvis, as shown in FIG. 1. The dynamic reference frame 54 can be affixed to the patient's skin, by way of a selected adhesive patch and/or a tensioning system. The dynamic reference frame 54 may also be removably attachable to fiducial markers 60 also positioned on the patient's body and further discussed herein. The dynamic reference frame 54 can also be connected to a bone portion of the anatomy. The bone portion can be adjacent, the area of the procedure, the bone of the procedure, or any appropriate bone portion.

The dynamic reference frame 54 may also be attached to various boney portions such as a femur, pelvis, cranium, or other boney portions. The movement of various portions, such as the instrument 52, relative to these boney portions can then be determined, even if the boney portion is also moved. This may assist in positioning an implant or in performing a planned procedure.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the instrument 52 or a pointing device or probe 66 is used, the work station 34 in combination with the coil array controller 48 and the C-arm controller 28 uses the translation map to identify the corresponding point on the pre-acquired image or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy and the position of the instrument 52 or attachment member attached to the instrument 52. Knowing the location of these two items allows the navigation system 10 to compute and display the position of the instrument 52 in relation to the patient 14. The tracking system 44 is employed to track the instrument 52 and the anatomy simultaneously.

The tracking system 44, if it is using an electromagnetic tracking assembly, essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the instrument 52 by measuring the field strength at the tracking sensor 58 location. The dynamic reference frame 54 is fixed to the patient 14 to identify the location of the patient in the navigation field. The electromagnetic tracking system 44 continuously recomputes the relative position of the dynamic reference frame 54 and the instrument 52 during localization and relates this spatial information to patient registration data to enable image guidance of the instrument 52 within and/or relative to the patient 14.

Patient registration is the process of determining how to correlate the position of the instrument 52 relative to the patient 14 to the position on the diagnostic or pre-acquired images. To register the patient 14, a physician or user 67 may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54, such as those disclosed in U.S. Pat. No. 6,381,485, entitled "Registration of Human Anatomy Integrated for Electromagnetic Localization," issued Apr. 30, 2002, herein incorporated by reference.

The system 10 may also perform registration using anatomic surface information or path information as is known in the art. The system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient and patient space. Generally, the navigation system allows the images on the display 36 to be registered and accurately display the real time location of the various instruments, such as the instrument 52, and other appropriate items, such as the pointer 66. In addition, the pointer 66 may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 36.

With additional reference to FIG. 3, the dynamic reference frame 54 can be affixed to any appropriate portion of the patient 14, and can be used to register the patient to the image data, as discussed above. For example, when a spinal procedure is being performed, the dynamic reference frame 54 can be interconnected with a portion of a spine 15 of the patient. The spine 15 can include various vertebral bodies 15a and portions of the vertebral bodies. In addition, or alternatively, the dynamic reference frame 54 can be affixed to any appropriate portion of the patient 14. The dynamic reference frame 54 can be interconnected with a portion of a pelvis 17 of the patient 14. The dynamic reference frame 54 can be interconnected with the pelvis 17 in any appropriate manner, such as those discussed herein according to various embodiments.

Affixing the dynamic reference frame 54 to the pelvis can be appropriate if the procedure being performed is performed in a portion of the anatomy that is held substantially still or stable relative to the pelvis 17. For example, various portions of the lumbar spine 15 are held substantially constant relative to the pelvis 17. In other words, if the pelvis 17 moves a selected amount, the selected lumbar vertebrae 15a are held at a substantially constant distance relative to the pelvis 17. Therefore, it would be understood that the dynamic reference frame 54 can be interconnected with any selected portion of the anatomy.

To obtain a maximum reference it can be selected to fix the dynamic reference frame 54 in each of at least 6 degrees of freedom. Thus, the dynamic reference frame 54 can be fixed relative to axial motion X, translational motion Y, rotational motion Z, yaw, pitch, and roll relative to the portion of the patient 14 to which it is attached. Any appropriate coordinate system can be used to describe the various degrees of freedom. Fixing the dynamic reference frame relative to the patient 14 in this manner can assist in maintaining maximum accuracy of the navigation system 10.

With additional reference to FIG. 3, a dynamic reference frame fixation device 80 according to various embodiments is illustrated. The dynamic reference frame fixation device 80 generally includes a body 82 that extends between a first or proximal end 84 and a distal or second end 86. Extending from the distal end 86 is a bone engaging or fixation section 88. The bone engaging section 88 can be provided to engage a selected portion of the bone or another portion of the anatomy, such as the pelvis 17. It will also be understood that the bone engaging portion 88 can be provided to engage a portion of the anatomy other than bone.

The bone engaging section 88 can be formed in any appropriate manner, but can include at least a first arm or portion 90 and a second arm or portion 92 and may also include a third arm portion 94 and a fourth arm portion 96. Generally, at least two of the arm portions 90 and 92 can be provided. Though any appropriate number, such as the third and fourth arm portions 94, 96, or more can also be provided. The arm portions 90-96 engage the bone, such as the pelvis 17 can resist rotation of the dynamic reference frame fixation member 80.

Further, a distal end 98 of the bone engaging section 88 can be formed in any appropriate manner. Generally, the distal end 98 can be sharpened, such that the dynamic reference frame fixation member 80 can be driven into the selected bone portion, such as with a hammer. The bone engaging section can be sharpened in any appropriate manner so that a generally straight axial motion can drive the dynamic reference frame fixation member 80 into the bone. In other words, the distal end 98 can allow the dynamic reference frame fixation member 80 to be driven into the bone with a hammer or similar device, such that a rotation of the dynamic reference frame fixation member 80 is not required.

The body 82 can include any appropriate dimension, which may be a similar dimension to the bone engaging section 88. For example, the bone engaging section 88 can include a large or largest dimension A that defines the width between the ends of the first arm 90 and the third arm 94. Nevertheless, if two arms, such as arm 90, 92 are provided at substantially right angles to one another, the largest dimension may be smaller than the dimension A. Nevertheless, the dimension A may be about 1.5 mm to about 10 mm.

The dimension A can also be the largest dimension in the body 82. This can allow the dynamic reference frame fixation member 80 to be passed through a small incision or puncture wound in a soft tissue of the patient 14. This can allow the dynamic reference frame fixation member 80 to be implanted or positioned substantially percutaneously or through a very small incision. Also, as discussed herein, the dynamic reference frame fixation member 80 can be positioned in the anatomy through a puncture wound formed with a dilator and cannula.

Further, near the proximal end 84 of the body 82, a dynamic reference frame holding portion 100 can be provided. The dynamic reference frame holding portion 100 can include a bore or opening 102 that can selectively engage the tracking sensor 54a. Further, the dynamic reference frame holding section 100 can include a second bore 104 to further fix the tracking sensing 54a. Further, or in addition to the tracking sensor 54a, the integral or included tracking sensor that can act as a tracking sensor 54aa can be included in the body 82. The included tracking sensor 54aa can be an electromagnetic tracking sensor. The included or one piece tracking sensor 54aa can act as the tracking sensor for the dynamic reference frame so that an additional one need not be interconnected with the body 82. Nevertheless, it will be understood that any appropriate tracking sensor can be used as the dynamic reference frame, such as an electromagnetic tracking sensor, an acoustic tracking sensor, a nuclear tracking sensor, an optical or IR tracking sensor, or combinations thereof. The dynamic reference frame positioning member 80 can be provided to interconnect the dynamic reference frame with the bony portion, regardless whether the dynamic reference frame is selectively interconnected with the body 82 or formed with or in the body 82.

If the tracking sensor 54a is provided it can be interconnected with the dynamic reference frame holding portion 100. For example the tracking sensor can be formed as a shape that compliments the dynamic reference frame holding portion 100 such that positioning the tracking sensor 54a into the dynamic reference frame holding portion 100 fixes it relative to the body 82. Further, screws or pins can be provided to further interconnect the tracking sensor 54a with the dynamic reference frame holding portion 100. Alternatively, the locking screw 170 (FIG. 6) can engage any appropriate of the bores 102, 104 to fix the tracking sensor 54a relative to the body 82.

With reference to FIG. 4, a dynamic reference frame positioning member 110 according to various embodiments is illustrated. The dynamic reference frame positioning member 110 includes portions that are similar to those illustrated in the dynamic reference frame positioning member 80 illustrated in FIG. 3 and like reference numerals are used to reference like portions.

Extending from the distal end 86 of the dynamic reference frame positioning member 110 is a bone engaging section or portion 112. The bone engaging section 112 can include a extending member 114 that extends from the distal end 86. The extending member 114 can include a substantially smooth portion 116 and a second portion 118 from which bone engaging fins 120, 122, 124, and 126. It will be understood, similar to the bone engaging portion 88, that any appropriate number of fins may be provided and four is merely provided as an example. The smooth portion 116 can terminate in a blunted or sharpened end.

The bone engaging portion 112 can be driven into the bone similar to the bone engaging portion 88. Therefore, the smooth end 116 may include a sharpened or bone driving portion so that the dynamic reference frame positioning member 110 can be driven into a selected portion of the anatomy, such as the pelvis 17. Similar to the bone engaging portion 88, the bone engaging portion 112 can allow the dynamic reference frame positioning member 110 to be hammered or impacted to be driven axially into the bone. Therefore, the dynamic reference frame positioning member 110 need not be screwed or rotated to drive the dynamic reference frame positioning member 110 into the bone. The various fins 120, 122, 124, 126 can be sharpened on the distal portion thereof to assist in driving the dynamic reference frame positioning member 110 into the selected portion of the anatomy.

Further, the various fins 120, 122, 124, 126 can engage the bone to substantially resist rotation of the dynamic reference frame positioning member 110 after insertion thereof. Therefore, the tracking sensor 54a, 54aa interconnected with the dynamic reference frame positioning member 110 can be held relative to the bone in a selected manner, such as to resist rotation, translation, axial movement, and movement in pitch, yaw, and roll. Also the dynamic reference frame positioning member 110 can have an included or one piece tracking sensor 54aa, similar to that of the dynamic reference frame positioning member 80. Thus, the separate or modular tracking sensor 54a may not be used. Further, either or both of the dynamic reference frames can be any appropriate tracking sensor, such as those discussed above and herein.

With reference to FIG. 5, a dynamic reference frame positioning member 130 is illustrated. The dynamic reference frame positioning member 130 includes a body 132 that extends between a first or distal end 134 and a second or proximal end 136. Near the second end 136 is a dynamic reference frame positioning portion 135. The dynamic reference frame positioning portion 135 can be formed in any appropriate manner, such as the dynamic reference frame positioning portion 100 illustrated in the dynamic reference frame positioning members 80, 110. Nevertheless, the dynamic reference frame positioning portion 135 can include a selected geometry, such as a hexagon, square, cylindrical or the like, that can be interconnected with the tracking sensor 54a, such as that discussed herein. For example the locking screw 170 (FIG. 6) can contact one of the flats of the dynamic reference frame positioning portion 135 to holding the tracking sensor 54a relative thereto. Although it will be understood that an included or one-piece tracking sensor 54aa may be provided in the dynamic reference frame positioning member 130.

The dynamic reference frame positioning member 130 also includes a bone engaging portion 138 that extends from the first end 134. Similar to the bone engaging portion 88, the bone engaging portion of 138 can include any appropriate number of fins 138 such as a first fin 138a, a second fin 138b, a third fin 138c and a fourth fin 138d. It will be understood that any appropriate number of the fins 138 can be provided. The fins 138 can include sharpened edges and sharpened ends to assist in their movement into a selected bone portion. As discussed herein, the dynamic reference frame positioning member 130 may be driven substantially axially, such as with an impacting motion, into the selected bone portion. Further, as discussed herein, the selected number of fins or geometry of the fins 138 can provide for a reduction or elimination or rotation of the dynamic reference frame positioning member 130.

It will be understood that the dynamic reference frame positioning members 80, 110, 130, can be used according to any appropriate embodiments and any selected procedure. Further, the selection of the dynamic reference frame positioning member 80, 110, 130 can be for the procedure, selection by a user, inclusion of the selected kit, or the like. Therefore, it will be understood that the dynamic reference frame positioning member 80, 110, 130 can be used according to any appropriate reason.

The dynamic reference frame positioning members 80, 110, 130 can interconnect a selected tracking sensor, such as an optical reflective tracking sensor 54a or an electromagnetic tracking sensor 54aa that can be interconnected or formed in the body 82, relative to the anatomy. Therefore, the dynamic reference frame positioning members 80, 110, 130 can be driven through substantially small or puncture wounds of the soft tissue to engage a selected portion of the anatomy, especially bony portions therein. This can allow the tracking sensor 54a, 54aa to be held relative to a selected portion of the anatomy by providing the dynamic reference frame positioning member 80, 110, 130 through a small incision with a hammer force or other similar force producing device.

It can also be understood, according to various embodiments, that registration techniques can be used to determine the position of the dynamic reference frame 54 relative to any portion of the selected dynamic reference frame positioning member 80, 110, 130. For example the probe 66 can be tracked and touched to the first end of the respective dynamic frame positioning member 80, 110, 130 so that the navigation system 10 can determine the position of the anatomy. Alternatively, or in addition there to, such information can be preprogrammed or stored in the navigation system 10.

Also, the dynamic reference frame 54 can include a fiducial portion. The fiducial portion can be formed into the tracking sensor 54a, the dynamic reference frame positioning member 80, 110, 130, or any appropriate portion. For example a dimple can be formed in the dynamic reference frame that the probe 66 can touch. This can allow for registration of the patient space to the image space. Further, it will be understood that the fiducial portion of the dynamic reference 54 can be formed with or separate from any other portion of the dynamic reference frame.

Figure 6:
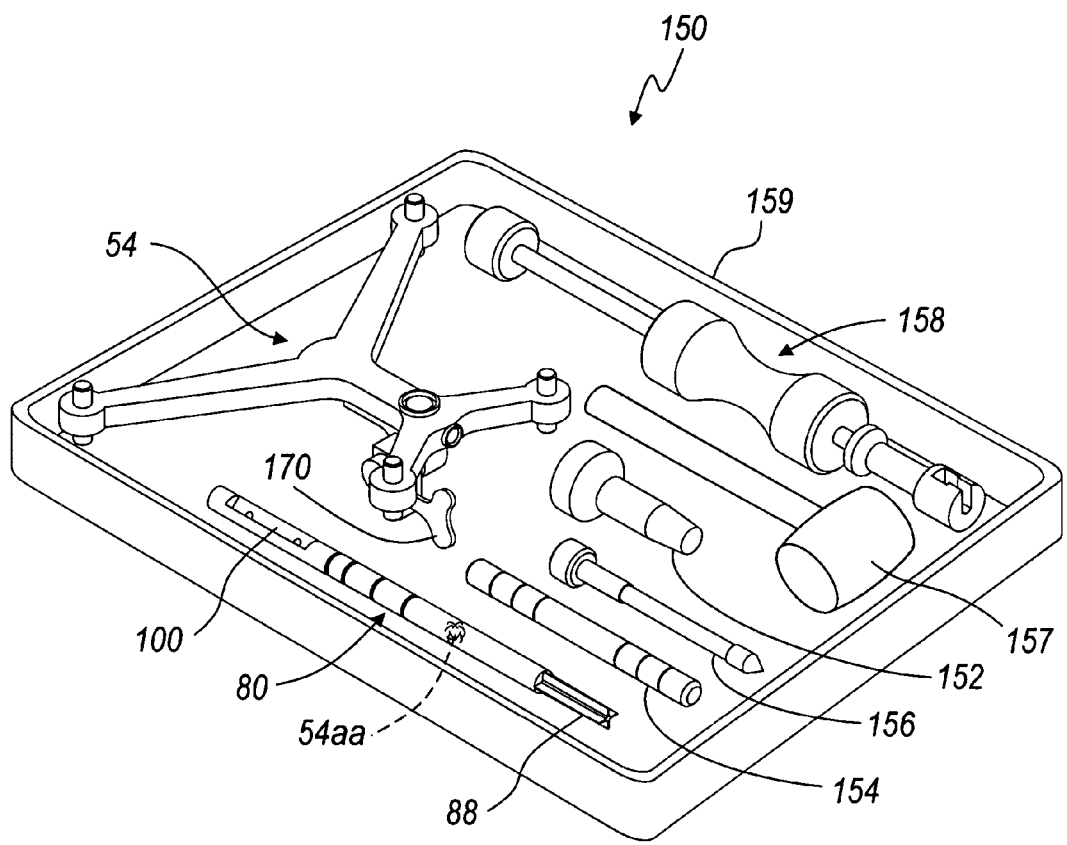
FIG. 6 is a kit including various instruments to perform a procedure according to various embodiments.

With reference to FIG. 6, the dynamic reference frame positioning member 80 can be provided in a kit 150 that can include a plurality of instruments or portions. It will be understood that the kit 150 can be understood as a system for positioning the dynamic reference frame 54 and/or a part of the navigation system 10. Further, the kit 150 can include all, part, or more parts than those illustrated and discussed. It will be understood that the dynamic reference frame positioning member 110 and/or 130 can also be provided in addition to or in the alternative of the dynamic reference frame positioning member 80, and only one is shown for clarity of the following discussion. The various portions included in the kit 150 can include any appropriate portions, and only exemplary include those described herein. Therefore, it will be understood that the portions of the kit 150 described herein are merely exemplary and not intended to limit the scope of the present teachings.

Regardless the kit 150 can include the dynamic reference frame positioning member 80 (which can also be referenced as a percutaneous reference pin). Further, the kit 150 can include the tracking sensor 54a, which can be interconnected with the dynamic reference frame positioning member 80. It will be understood, however, that the dynamic reference frame positioning member 80 may have included therein the tracking sensor 54aa.

The kit 150 may also include a tap cap 152, a cannula 154, a dilator 156, an impactor 157, and a slap hammer 158. The various portions of the kit 150 can be used according to any appropriate embodiment. Further, the portions of the kit 150 can be selected to include selected features. For example the cannula 154 can be flexible, rigid, or a combination thereof. Also, the kit 150 may be used according to a method as exemplary described herein. Therefore, it will be understood that the portions of the kit 150 may be used with any appropriate system or method and the method described herein is merely exemplary.

It will be understood that each of the portions of the kit 150 may be substantially single use and can be disposed of after a selected procedure. Nevertheless, it will be understood that the various portions of the kit 150 may also be multi-use and used for a plurality of procedures. Regardless, various portions of the kit 150, such as the dynamic reference frame positioning member 80, can be formed of any appropriate materials, such as various metals or metal alloys, polymers, or any other appropriate materials. The various portions of the kit 150, such as the dynamic reference frame positioning member 80 can be sterilized according to various procedures to reduce or eliminate the possibility of contamination or infection during use. Further the kit 150 can be provided in a container 159 that can be sterilized with each of the portions included therewith. Also the kit 150 can be provided in a sterile manner such that no additional procedures need to occur to provide a sterile kit.

Figure 7:
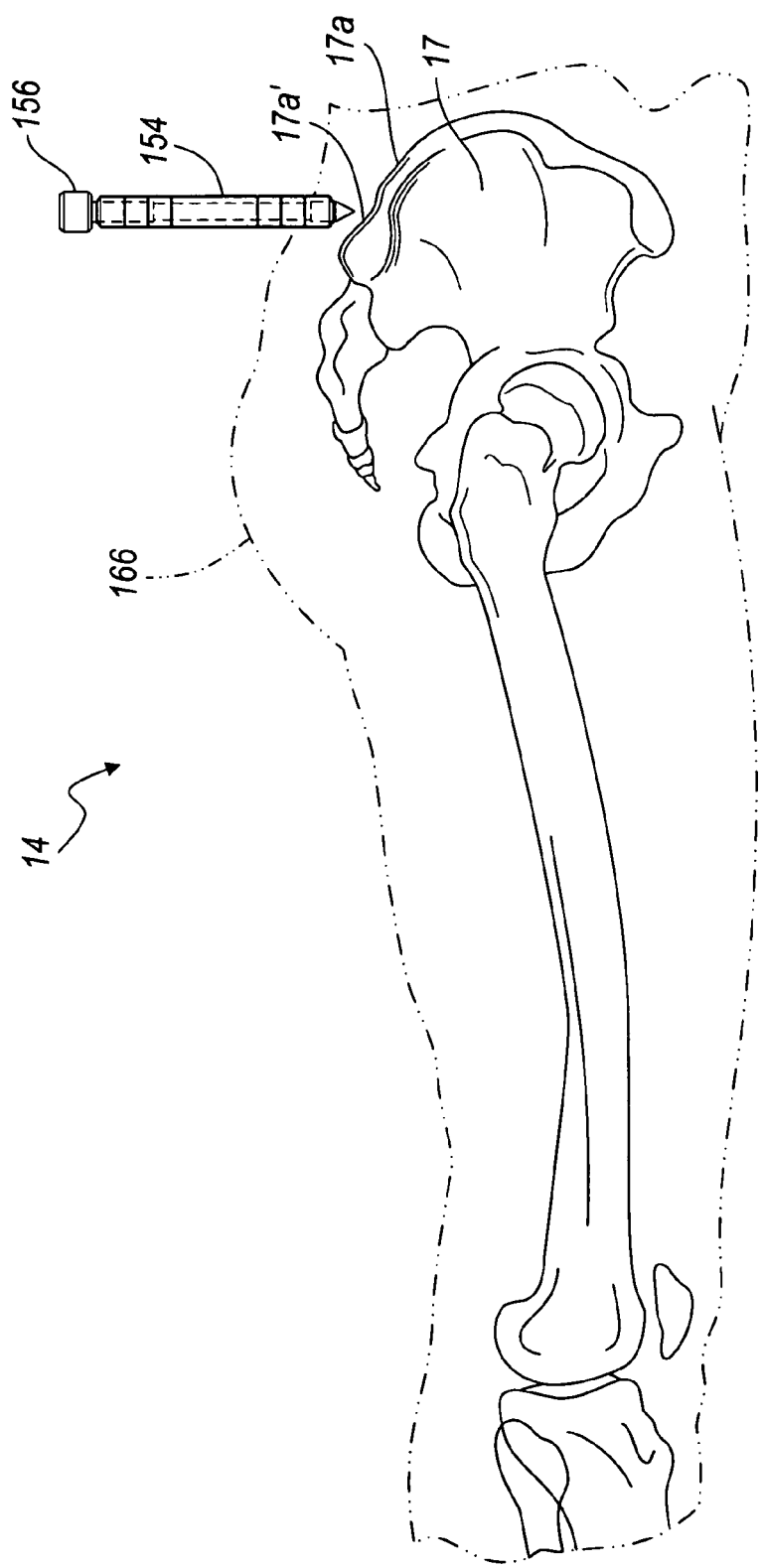
FIG. 7 is an environmental view of a dilator and cannula.
Figure 8:
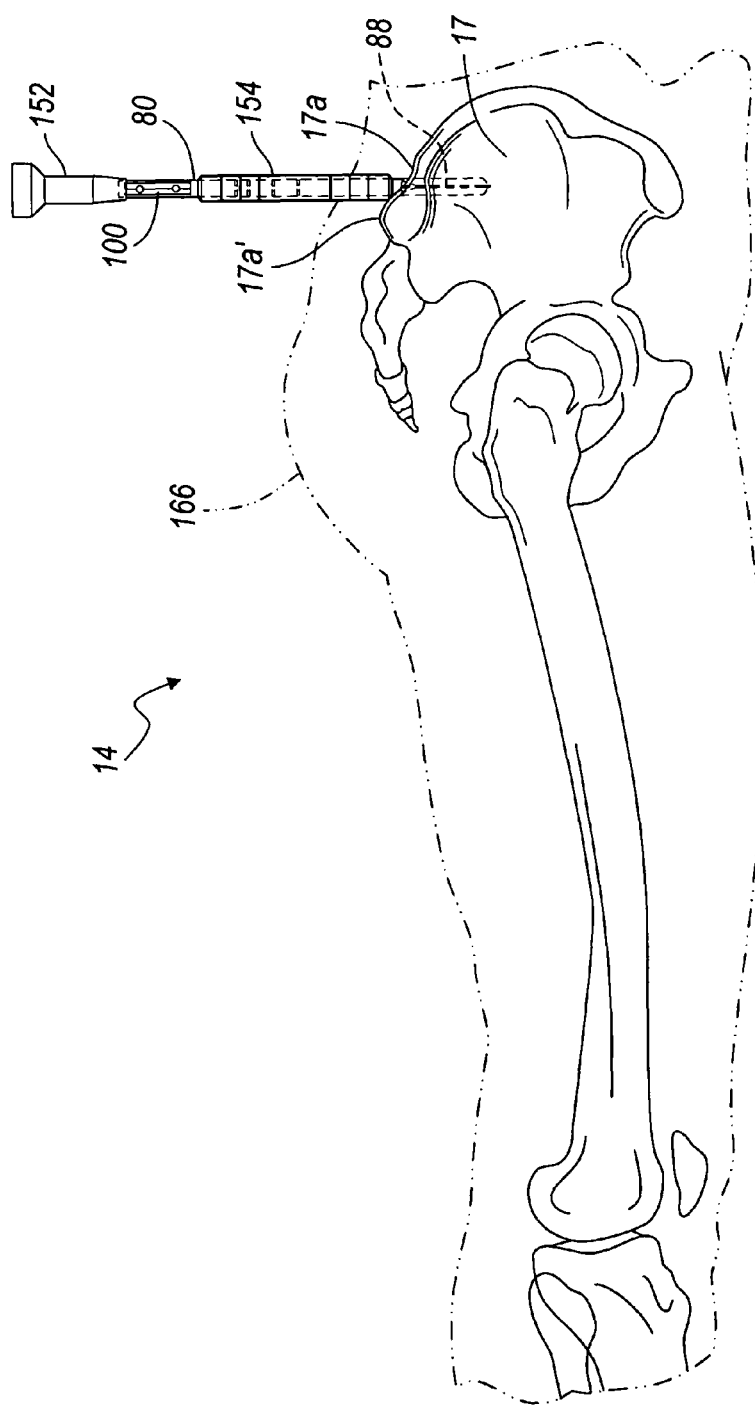
FIG. 8 is an environmental view of positioning a positioning member according to various embodiments.
Figure 9:
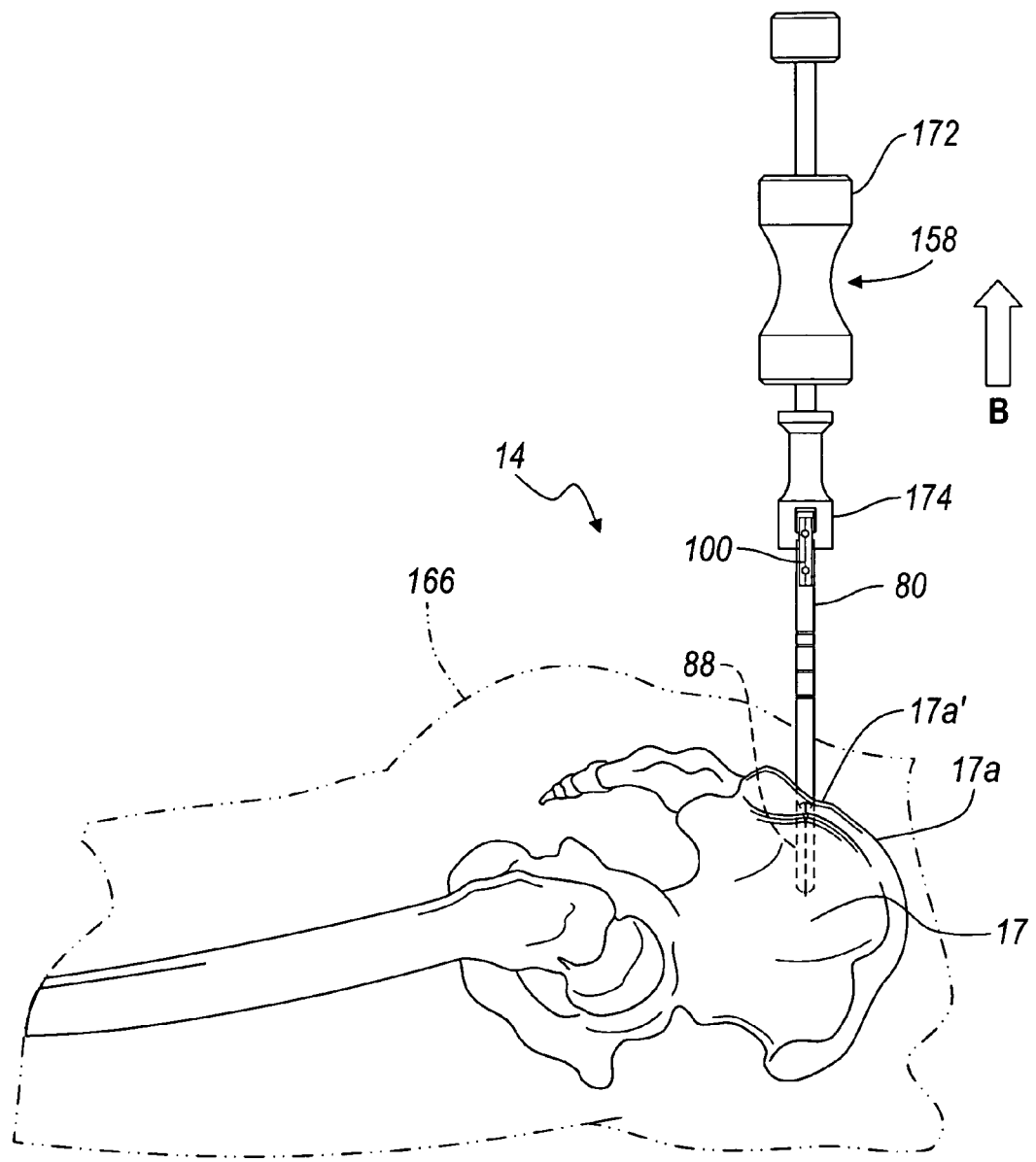
FIG. 9 is an environmental view of the removal of a positioning member according to various embodiments.

According to a selected procedure or illustrated in FIGS. 7-9, the dynamic reference frame positioning member 80 can be inserted into a selected portion of the anatomy. A small or stab incision can be formed in an appropriate portion of the anatomy, such as over the posterior superior iliac spine (PSIS) or crest 17a' or in any area relative to the pelvis 17 or the iliac crest 17a. The incision can be formed in any appropriate manner, such as with a scalpel or other appropriate instrument. The incision can also be formed with the dilator 156 and/or cannula 154 being pushed or moved through a skin and/or soft tissue layer 166.

With reference to FIG. 7, the cannula 154 can be placed percutaneously passed through a layer of soft tissue, including skin 166 into the iliac 17a. As discussed above, the iliac 17a generally includes a PSIS 17a. The PSIS 17a' can be accessed through a posterior portion of the patient 14 through the skin 166. The cannula 154 can be positioned percutaneously by positioning the dilator 156 through the cannula 154 and simultaneously inserting both members through the soft tissue, including the skin 166.

Both the dilator 156 and the cannula 154 can include cutting or puncturing edges, which allow it to be passed through the soft tissue, including the skin 166. Positioning the dilator 156 through the cannula 154 can assist in assuring that no soft tissue or other material passes into the cannula 154 prior to a selected procedure. Further, the use of the dilator 156 with the cannula 154 can substantially eliminate the necessity of forming any other incisions through the soft tissue including the skin 166 to position the cannula 154 relative to the PSIS 17a'. The use of the cannula 154 and the dilator 156 allows for an ease of the operation further discussed herein.

Once the cannula 154 is positioned next to or relative to the PSIS 17a', the dilator 156 can be removed from the cannula 154. Once the dilator is removed from the cannula 154, the bore defined by the cannula 154 can be used to position a selected member relative to the PSIS 17a'. The portion to be positioned can include the dynamic reference frame positioning member 80. It will be understood that the present exemplary method discusses specifically the dynamic reference frame positioning member 80, but any appropriate member may be used such as the dynamic reference frame positioning members 110, 130.

The dynamic reference frame positioning member 80 can be passed through the cannula 154 until it engages or touches the PSIS 17a'. The dynamic reference frame positioning member 80 can then be driven into the PSIS 17a' in any appropriate manner. It will be understood that any other appropriate preparatory steps may also occur. For example, a pilot or preformed hole may be made in the pelvis 17 prior to positioning the dynamic reference frame positioning member 80. This can allow the dynamic reference frame positioning member 80 to be driven through the pilot hole formed in the pelvis 17. it will be understood, however, that a pilot hole or other preformed opening is not necessary and is described merely as an example.

The tap cap 152 can be selectively interconnected with the dynamic reference frame positioning member 80 and be used, with the impactor 157 to drive or impact the dynamic reference frame positioning member 80 into the PSIS 17a'. Any appropriate instrument can be used to assist in this procedure, such as the hammer or mallet 157. The hammer 157 can be used to impact the proximal or exposed end of the tap cap 152 to drive the dynamic reference frame positioning member 80 into the bone.

The dynamic reference frame positioning member 80 can be driven in any appropriate distance, such as until the tap cap 152 engages a portion of the cannula 154. Also, the body 82 of the dynamic reference frame positioning member 80 can include selected indicia or markings to assist in determining an amount of movement of the dynamic reference frame positioning member 80 relative to the cannula or the patient 14. Therefore, it will be understood that the bone engaging portion section 88 of the dynamic reference frame positioning member 80 can be determined to be positioned if the body 82 of the dynamic reference frame positioning member 80 is substantially similar in length to the cannula 154. It will be understood, however, that any appropriate system may be used to determine appropriate positioning of the dynamic reference frame positioning member 80.

Once the dynamic reference frame positioning member 80 has been driven into the PSIS 17a', the tracking sensor 54a can be interconnected with the dynamic reference frame positioning member 80. It will be understood, however, that the cannula 154 and/or the tap cap 152 can also be removed before interconnecting the tracking sensor 54a with the dynamic reference frame positioning member 80. Therefore, for a majority of the procedure, only the dynamic reference frame positioning member 80 is provided percutaneously to engage the PSIS 17a'.

Also, prior to impacting the dynamic reference frame positioning member 80 a fiducial may be used to determine an appropriate location. Further the dynamic reference frame positioning member 80 may act as a fiducial that is positioned when image data is collected regarding the patient. Thus the tracking sensor 54a need only be connected to the dynamic reference frame positioning member 80 during an operative procedure. Thus the dynamic reference frame positioning member 80 can be a fiducial for use in registering the image data or image space to patient space.

Further, if the integral tracking sensor 54aa is provided, driving the dynamic reference frame positioning member 80 into the PSIS 17a' may substantially complete positioning the dynamic reference frame. Nevertheless, if the tracking sensor 54a is provided, it can be selectively interconnected with the dynamic reference frame positioning member 80. When the tracking sensor 54a is used it can include a locking screw 170 that can engage the dynamic reference frame positioning portion 100. As discussed above, the dynamic reference frame positioning portion 100 can include a bore 102, which the locking screw 170 may engage. The tracking sensor 54a can include other positioning portions, such as an angle screw, a translation screw, or the like, which can allow for adjustment or positioning the tracking sensor 54a in any of the 6 degrees of freedom or any selected number thereof. Nevertheless, the tracking sensor 54a can be interconnected with the dynamic reference frame positioning member 80 in any appropriate manner.

Once the tracking sensor 54a is interconnected with the dynamic reference frame positioning member 80, (as illustrated in FIG. 1) if necessary, the tracking sensor 54a can be localized or registered with the navigation system 10. It will be understood that the tracking sensor 54a can be any appropriate dynamic reference frame, such as an optical dynamic reference frame, an electromagnetic dynamic reference frame, or any appropriate dynamic reference frame. Regardless, the dynamic reference frame positioning member 80 allows the tracking sensor 54a, 54aa to be held at a selected location relative to a portion of the anatomy for a period during the procedure. The bone engaging portion 88, according to various embodiments, can substantially reduce or eliminate rotation of the dynamic reference frame positioning member 80, and therefore, the tracking sensor 54a. Further, the bone engaging portion 88 can also substantially reduce or eliminate translation or axial movement of the dynamic reference frame positioning member 80 and, consequently, motion of the tracking sensor 54a. Therefore, the dynamic reference frame positioning member 80 can allow for percutaneous holding of the tracking sensor 54a relative to the patient 14 for a selected procedure. The dynamic reference frame positioning member 80 can hold the tracking sensor 54a, 54aa in any selected amount, such as in six degrees of freedom including rotation, translation, axial motion, roll, pitch, and yaw.

After a selected procedure is performed, such as a disc replacement, nucleus replacements, vertebral implants, or other appropriate procedures, the dynamic reference frame positioning member 80 and the tracking sensor 54a, 54aa can be removed.

Although the tracking sensor 54a and the dynamic reference frame positioning member 80 can be removed in any appropriate manner, the following is an exemplary method. Additionally, if provided, the tracking sensor 54a can be disconnected from the dynamic reference frame positioning member 80. The locking screw 170 can be loosened or disconnected to allow for removal of the tracking sensor 54a. If the tracking sensor 54aa is provided, the tracking sensor 54a need not be present and may not need to be removed.

After the tracking sensor 54a, if provided, is removed the slap hammer 158 can engage a portion of the dynamic reference frame positioning member 80, as illustrated in FIG. 9, such as the dynamic reference frame engaging portion 100 of the dynamic reference frame positioning member 80. Once the slap hammer 158 has appropriately engaged the dynamic reference frame positioning member 80, the slap hammer 158 can be operated in an appropriate manner to remove the dynamic reference frame positioning member 80.

The slap hammer 158 can include a handle 172 that can be operated by a user, such as a physician. An engaging end 174 is provided to engage the dynamic reference frame positioning member 80 in a selected manner. The handle 172 can be moved in the direction of arrow B to provide an axial movement of the slap hammer to withdraw the dynamic reference frame positioning member 80 from the PSIS 17a'. Once the dynamic reference frame positioning member 80 has been removed from the PSIS 17a', the dynamic reference frame positioning member 80 can be disposed of in an appropriate manner or cleaned and sterilized for further procedures.

Therefore, as discussed above, the dynamic reference frame 54 can be positioned relative to a selected portion of the patient 14 substantially percutaneously, such as through a puncture or through a small incision. The small incision can be closed in any appropriate manner, with or without sutures.

Regardless, the disruption of natural tissue with the use of the dynamic reference frame positioning member 80, 110, 130 according to various embodiments is substantially minimal. Therefore recovery time due to the positioning of the dynamic reference frame 54 can be substantially reduced or eliminated. Also, the ability to drive a dynamic reference frame positioning member 80 substantially axially into the bone, such as the iliac 17 can provide for ease of use by a user, such as a physician, and also further reduce trauma to the soft tissue surrounding the area of positioning of the dynamic reference frame positioning member 80. This can further assist in reducing trauma to the patient 14 and assist in speeding recovery.

It will be understood, that the dynamic reference frame positioning member 80 can be used to position any appropriate modular tracking sensor 54a or can include the integral tracking sensor 54aa. As discussed above, the modular tracking sensor 54a can be an optical, electromagnetic, acoustic, or any other appropriate dynamic reference frame. Further, the modular tracking sensor 54a can be formed in any appropriate geometry for selected instrumentation. The modular tracking sensor 54a, using the dynamic reference frame positioning member 80, can be used to perform any appropriate procedure and can be used to track to any appropriate portion of the anatomy.

For example, the dynamic reference frame positioning member 80 can be driven into the iliac crest, such as that described above, driven into a portion of the leg, such as a portion of the femur, driven into a portion of the arm, such as the humerus, or the like. The dynamic reference frame positioning member 80, 110 can be sized to allow it to be interconnected with any appropriate portion of the anatomy and driving it into the iliac crest is merely exemplary. Regardless, the dynamic reference frame 54 can be positioned relative to a selected portion of the anatomy to allow for referencing or dynamically tracking a portion of the anatomy during a procedure.

Figure 10:
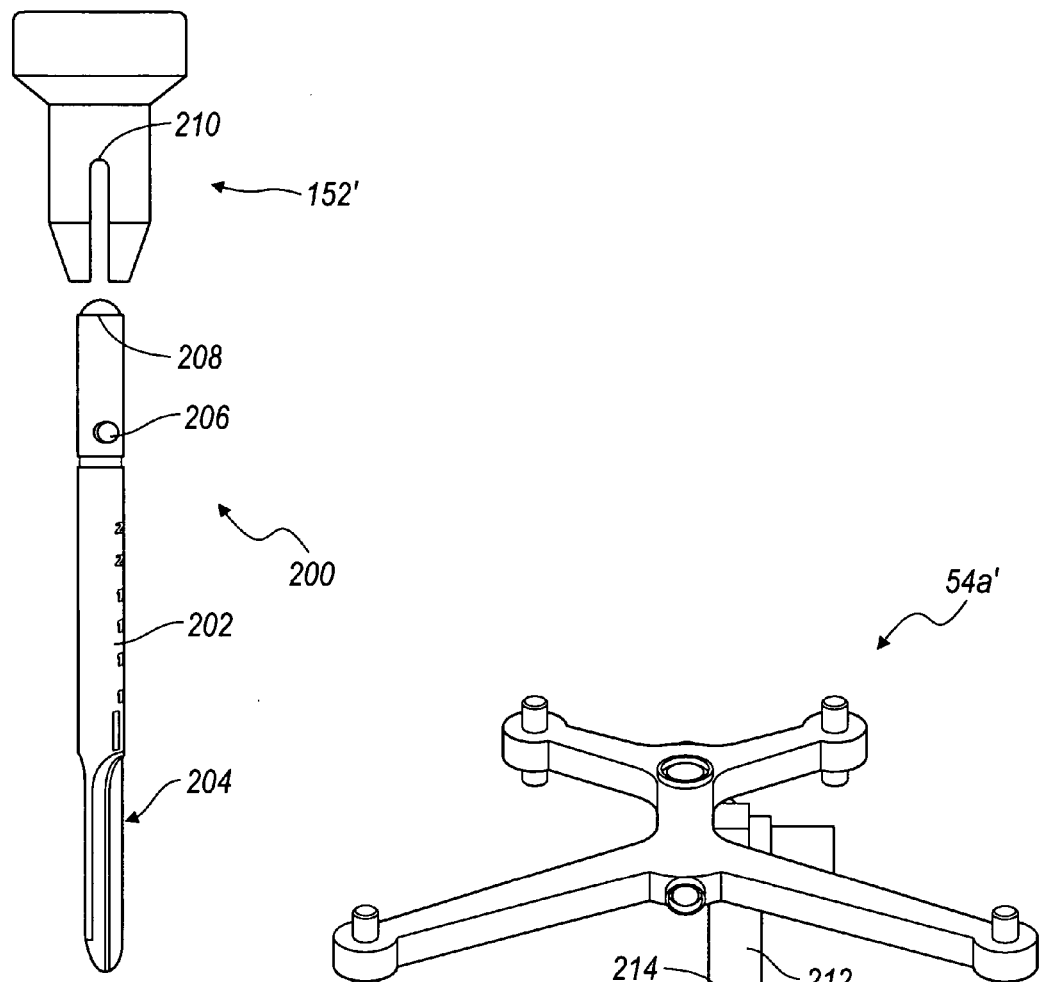
FIG. 10 is a positioning member and tap cap according to various embodiments.
Figure 11:
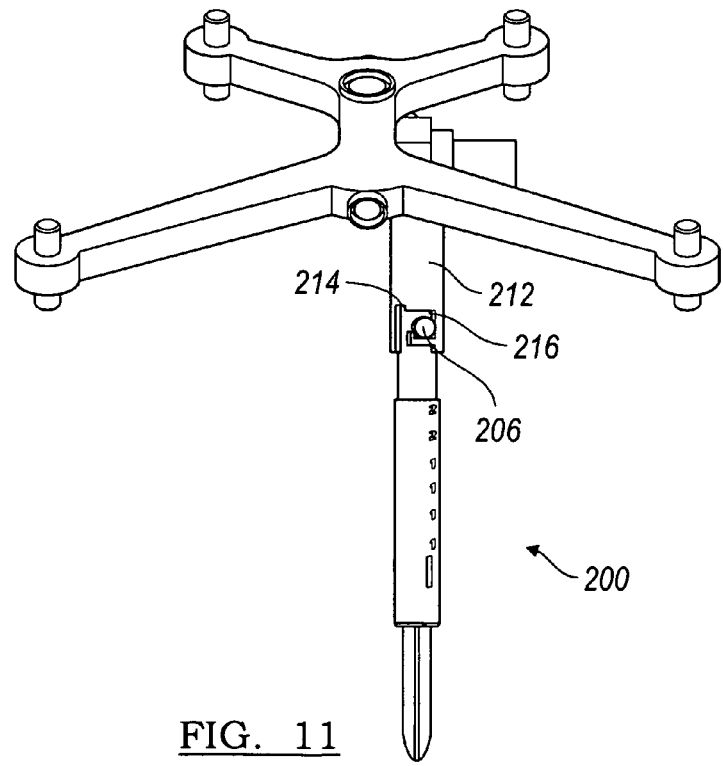
FIG. 11 is a modular tracking sensor connected to a positioning member according to various embodiments.

Turning to FIGS. 10 and 11, a dynamic reference frame holding member 200 according to various embodiments is illustrated. The dynamic reference frame holding member 200 can include a plurality of portions that are similar to the previously disclosed dynamic reference frame holding members 80, 110, 130. The similar portions will not be described in detail here as they will be understood by one skilled in the art. Briefly, however, the dynamic reference frame holding member 200 can include a shaft 202 extending between two ends. Near a first end, a bone engaging portion 204 can be formed. The bone engaging portion 204 can include any appropriate engaging portion such as a plurality of fins, points and the like. Nevertheless, the bone engaging portion 204 can hold the dynamic reference frame holding member 200 relatively fixed to the anatomy 14 in translation, axial movements, rotation, yaw, pitch, and roll.

Near the second end of the shaft 202 is a resiliently deformable member 208, such as a spring, a rubber component, or other similar resilient members. Further, an engaging pin 206 is formed to extend from the shaft 202. It will be understood that the engaging pin 206 can extend from a plurality of positions or include a plurality of extending portions. Nevertheless, a single extending portion is illustrated for clarity of the current discussion.

The dynamic reference frame holding member 200 can be inserted in a manner substantially similar to that discussed above. Nevertheless, a tap cap 152' can include a slot or passage 210 that is able to extend over a proximal or second end of the dynamic reference frame holding member 200 so as not to engage the engaging pin 206 in a substantial manner. Therefore the tap cap 152' can engage mostly the resilient portion 208 rather than directing forces on the engaging pin 206. Therefore the dynamic reference frame holding member 200 can be driven into a selected portion of the anatomy, such as the PSIS 17a' as discussed above. The dynamic reference frame holding member 200 can include an integral or single piece tracking sensor 54aa. Nevertheless, the engaging pin 206 can be used to engage a modular tracking sensor 54a' illustrated in FIG. 11. The modular tracking sensor 54a' can include an engaging shaft 212 that can include a portion that is operable to move over or pass over the second end of the dynamic reference frame holding member 200. An opening 214 can be defined in the shaft portion 212 of the modular tracking sensor 54a' to allow the engaging pin 206 to move into a selected portion of the opening 214.

When positioning the tracking sensor 54a' relative to the dynamic reference frame holding member 200, the tracking sensor 54a' can have a force applied to it to deform the resilient member 208. The modular tracking sensor 54a' can then be rotated to move the engaging pin 206 to a selected portion of the opening 214. Once the engaging pin 206 is positioned in a selected area of the opening 214, the applied force to the modular tracking sensor 54a' can be removed. The resilient member 208 can then push against the modular tracking sensor 54a' to move the modular tracking sensor 54a' in a manner that allows the engaging pin 206 to engage in an engaging portion 216 of the opening 214.

Therefore the modular tracking sensor 54a' can be easily and quickly interconnected with the dynamic reference frame holding member 200. Further, the modular dynamic reference frame 54a' can be easily and repeatedly interconnected with the dynamic reference frame holding member 200 during a selected procedure prior thereto, or afterwards. The engaging pin 206, in cooperation with the resilient member 208 and the engaging section 216, can allow for ease of attachment in a quick manner. It also allows for ease of substantial repeatability of the engagement. Therefore, the modular tracking sensor 54a' can be easily interconnected with the holding member 200. Nevertheless, it will be understood that a modular tracking sensor can be interconnected with any appropriate dynamic reference frame holding member 80, 110, 130 for various purposes.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A surgical navigation system for use in a surgical procedure on an anatomy including a bone, comprising:
 a tracking system operable to track a tracking sensor;
 a surgical instrument operable to be tracked by said tracking system;
 a dynamic reference frame having the tracking sensor; and
 a dynamic reference frame positioning member extending along an axis from a first end to a second end;
 wherein said first end forms a one piece bone engaging portion having a first portion and a second portion extending at a fixed angle relative to one another;
 wherein the tracking sensor is tracked by the tracking system;
 wherein the dynamic reference frame positioning member is operable and configured to engage a bone in the anatomy and be axially impacted along the axis of the dynamic reference frame positioning member into the bone in a selectively fixed manner to hold said dynamic reference frame at a selected position; and
 wherein the tracking system is configured to correlate the surgical instrument relative to the dynamic reference frame.

2. The surgical navigation system of claim 1, wherein said dynamic reference frame positioning member positions said dynamic reference frame substantially immobile in rotational movement, axial movement, translational movement, yaw movement, pitch movement, and roll movement, or combinations thereof relative to the anatomy.

3. The surgical navigation system of claim 1, wherein said tracking system includes an electromagnetic tracking system, an optical tracking system, an infrared tracking system, an acoustic tracking system, or combinations thereof.

4. The surgical navigation system of claim 1, further comprising:
 an imaging system operable to obtain patient image data.

5. The surgical navigation system of claim 4, wherein said imaging system is selected from a group consisting of a C-arm, a fluoroscope, an MRI, a PET scanner, a computer tomography system, an x-ray system, an ultrasound system, and accommodations thereof.

6. The surgical navigational system of claim 4, further comprising:
 a monitor;
 wherein the image data is displayed on the monitor and said dynamic reference frame is tracked relative to said image data.

7. The surgical navigation system of claim 1, further comprise:
 at least one of a cannula, a dilator, a slap hammer, an impactor, a tap cap or combinations thereof.

8. The surgical navigation system of claim 1, further comprising a cannula operable to be passed through a selected portion of the anatomy relative to the bone in the anatomy:

wherein said dynamic reference frame positioning member is operable to be positioned relative to the bone with said cannula.

9. The surgical navigation system of claim 8, further comprising:
a dilator;
wherein said dilator is operable with said cannula to move the cannula through a selected portion of the anatomy.

10. The surgical navigation system of claim 1, wherein said surgical instrument is at least one of an impactor, a stylet, a reamer, a reamer driver, a probe, an implant positioning instrument, a tap, a drill, a drill bit, or combinations thereof.

11. The surgical navigation system of claim 1, wherein said dynamic reference frame further: includes a fiducial marker.

12. The surgical navigation system of claim 11, wherein said fiducial marker is integral with said dynamic reference frame.

13. The surgical navigation system of claim 1, wherein said tracking sensor of said dynamic reference frame is formed as a single member with said dynamic reference frame positioning member.

14. The surgical navigation system of claim 1, wherein said tracking sensor of said dynamic reference frame is selectively coupled to said dynamic reference frame positioning member.

15. The surgical navigation system of claim 1, wherein said tracking sensor is at least one of an electromagnetic tracking sensor, an optical tracking sensor, an infrared tracking sensor, an acoustic tracking sensor, a reflective tracking sensor, or combinations thereof.

16. The surgical navigation system of claim 1, wherein said tracking sensor transmits a signal to be tracked by said tracking system.

17. The surgical navigation system of claim 1, wherein said first portion and said second portion extending at a fixed angle relative to one another define a substantially cruciform cross-section.

18. The surgical navigation system of claim 1, wherein said first end further includes at least one of an extending portion with a smooth surface, said first portion and said second portion that terminate in sharpened ends, and said first portion and said second portion terminate in a substantially planar region.

19. A dynamic reference frame system operable to be fixed in a selected position relative to a bone, comprising:
a positioning member extending along an axis between a first end and a second end;
a tracking sensor engaging portion defined nearer said first end than said second end;
a resilient portion extending from said first end of said positioning member;
a catch member extending transverse to said axis and outwardly from said positioning member;
a tracking sensor defining a void in a connection portion and a finger extending into said void, wherein said finger selectively engages said catch member;
a bone engaging portion extending from near said second end;
wherein said resilient portion biases said finger towards said catch member;
wherein said bone engaging portion comprises a first member and a second member extending an angle relative to one another;
wherein said bone engaging portion is operable to be driven into the bone.

20. The dynamic reference frame system of claim 19, wherein said bone engaging portion further includes a third member and a fourth member;
wherein each of said first member, second member, third member, and fourth member are positioned at an angle of about 90 degrees relative to one another.

21. The dynamic reference frame system of claim 19, wherein said bone engaging portion further includes a central member.

22. The dynamic reference frame system of claim 21, wherein said first member and said second member extend from said central member.

23. The dynamic reference frame system of claim 19, further comprising:
an impactor;
wherein said bone engaging portion is driven into the bone with said impactor.

24. The dynamic reference frame system of claim 19, wherein said tracking sensor is at least one of an electromagnetic dynamic reference frame, an acoustic dynamic reference frame, a optical dynamic reference frame, a nuclear dynamic reference frame, or combinations thereof.

25. The dynamic reference frame system of claim 19, further comprising:
a slap hammer;
wherein said slap hammer is operable to remove said positioning member from the bone.

26. The dynamic reference frame system of claim 19, further comprising an imaging system operable to obtain an image data of a patient.

27. The dynamic reference frame system of claim 26, wherein the imaging system is at least one of a C-arm, a fluoroscope, an x-ray system, a magnetic resonance imaging system, an ultrasound system, a PET scanner, a computer tomography scanner, or combinations thereof.

28. The dynamic reference frame system of claim 26, further comprising:
a monitor.

29. The dynamic reference frame system of claim 28, further comprising a surgical instrument.

30. The surgical dynamic reference frame system of claim 29, further comprising a tracking system.

31. The dynamic reference frame system of claim 30, wherein said surgical instrument is tracked relative to the image data by maintaining a registration of the image data with the patient by tracking said tracking sensor.

32. The dynamic reference frame system of claim 19, wherein said bone engaging portion comprises a unitary member of the first member and the second member;
wherein the unitary member defines a substantially cruciform cross-section.

33. A dynamic reference frame system operable to be fixed in a selected position relative to a bone, comprising:
a positioning member extending between a first end and a second end;
a tracking sensor engaging portion defined nearer said first end than said second end;
a bone engaging portion formed by said second end;
a cannula; and
a dilator;
wherein said bone engaging portion comprises a first portion and a second portion extending at a fixed angle relative to one another and operable to be driven axially into the bone;
wherein said bone engaging portion is operable to be driven into the bone;

wherein said positioning member is operable to be moved through said cannula to engage the bone;
wherein said cannula is operable to be positioned relative to the bone initially with the dilator positioned through the cannula.

34. The dynamic reference frame system of claim 33, further comprising:
a tracking sensor interconnectable with said tracking sensor engaging portion.

35. The dynamic reference frame system of claim 34, wherein said tracking sensor is removable from said positioning member.

36. The dynamic reference frame system of claim 34, wherein said positioning member fixes said tracking sensor relative to the bone.

37. A method of using a dynamic reference frame system to position a dynamic reference frame relative to a selected portion of an anatomy including a bone, comprising:
positioning a cannula through a soft tissue portion of the anatomy relative to the bone portion, including:
passing a dilator through at least a portion of the cannula so that at least a portion of the dilator extends from an end of the cannula;
passing the cannula and dilator through the soft tissue, where the dilator assists in moving soft tissue for passage of the cannula; and
removing the dilator from the cannula to leave the cannula substantially free of obstruction;
passing the dynamic reference frame positioning member through said positioned cannula; and
impacting the dynamic reference frame positioning member along its long axis into engagement with the bone to fix the dynamic reference frame positioning member relative to the bone in at least one of a rotational motion, axial motion, translation motion, pitch movement, yaw movement, roll movement, or combination thereof.

38. The method of claim 37, further comprising:
positioning a first portion of the dynamic reference frame positioning member relative to a second portion of a dynamic reference frame positioning member to substantially eliminate rotation of the dynamic reference frame positioning member once fixed to the bone.

39. The method of claim 37, further comprising:
interconnecting a tracking sensor with the dynamic reference frame positioning member.

40. The method of claim 39, wherein fixing the tracking sensor to the dynamic reference frame positioning member includes:
affixing a tracking sensor selected from at least one of an acoustic dynamic reference frame, an electromagnetic dynamic reference frame, an optical dynamic reference frame, or combinations thereof.

41. The method of claim 39, further comprising:
tracking said tracking sensor with a tracking system.

42. The method of claim 41, wherein the tracking system is selected from at least one of an acoustic tracking system, an electromagnetic tracking system, a radiation tracking system, an optical tracking system, or combinations thereof.

43. The method of claim 37, further comprising:
removing the cannula;
wherein removing the cannula occurs after impacting the dynamic reference frame positioning member relative to the bone.

44. The method of claim 37, further comprising:
removing the dynamic reference frame positioning member from the bone.

45. The method of claim 44, wherein removing the dynamic reference frame positioning member from the bone includes interconnecting a slap hammer with the dynamic reference frame positioning member.

46. The method of claim 37, further comprising:
providing the dynamic reference frame positioning member with a bone engaging portion, including a first member and a second member extending at a fixed angle relative to one another.

47. The method of claim 37, further comprising obtaining image data of the anatomy.

48. The method of claim 47, wherein obtaining image data of the anatomy includes obtaining at least one of a two dimensional image data, three dimensional image data, four dimensional image data, or combinations thereof.

49. The method of claim 47, further comprising:
displaying the image data on a display viewable by a user.

50. The method of claim 49, further comprising:
tracking an instrument relative to the anatomy; and
displaying a representation of the position of the instrument relative to the anatomy on the display.

51. A method of using a surgical navigation system in a surgical procedure on an anatomy including a bone, comprising:
positioning a cannula through a soft tissue portion of the anatomy relative to the bone portion;
passing a single piece dynamic reference frame positioning member through said positioned cannula; and
striking the dynamic reference frame positioning member into engagement with the bone to fix the dynamic reference frame positioning member relative to the bone in at least one of a rotational motion, axial motion, translation motion, pitch motion, yaw motion, roll motion, or combination thereof;
removing the cannula through the soft tissue and away from said single piece dynamic reference frame positioning member;
after removing the cannula, interconnecting a tracking sensor directly to said single piece dynamic reference frame positioning member.

52. The method of claim 51, further comprising:
providing image data of the anatomy;
displaying the provided image data of the anatomy;
maintaining a registration of the image data with the anatomy.

53. The method of claim 51, wherein said tracking sensor is at least one of an electromagnetic tracking sensor, an acoustic tracking sensor, an optical tracking sensor, an infrared tracking sensor, or combinations thereof.

54. The method of claim 51, further comprising:
tracking a surgical instrument.

55. The method of claim 54, further comprising:
providing image data of the anatomy; and
displaying a representation of the surgical instrument relative to the provided image data.

56. The method of claim 51, further comprising:
removing the cannula.

57. The method of claim 51, further comprising:
providing the single piece dynamic reference frame positioning member as a unitary member.

58. A method of using a surgical navigation system in a surgical procedure on an anatomy including a bone, comprising:
positioning a cannula through a soft tissue portion of the anatomy relative to the bone portion;

passing dynamic reference frame positioning member through said positioned cannula; and impacting the dynamic reference frame positioning member into engagement with the bone to fix the dynamic reference frame positioning member relative to the bone in at least one of a rotational motion, axial motion, translation motion, pitch motion, yaw motion, roll motion, or combination thereof;

interconnecting a tracking sensor with said dynamic reference frame positioning member;

providing a resiliently deformable member extending from the dynamic reference frame positioning member;

providing an engaging member extending from the dynamic reference frame positioning member;

deforming the resilient deformable member with the tracking sensor with an applied force; and removing the applied force to allow the engaging member to engage the tracking sensor;

wherein the tracking sensor is resiliently interconnected with the dynamic reference frame positioning member.

59. The method of claim 58, wherein the resiliently deformable member moves the tracking sensor from an unengaged position to an engaged position when the applied force is removed.

60. The method of claim 58, further comprising:

applying the force relative to the dynamic reference frame positioning member to deform the resilient deformable member to a second orientation with the tracking sensor to move the tracking sensor from a first position to a second position relative to the dynamic reference frame positioning member; and wherein removing the applied force allows the resiliently deformable member to rebound towards the first orientation to allow the engaging member to engage the tracking sensor.

61. A surgical navigation system for use in a surgical procedure on an anatomy including a bone, comprising:

a tracking system operable to track a tracking sensor;

a dynamic reference frame having the tracking sensor;

a dynamic reference frame positioning member extending along an axis from a first end to a second end;

a tap cap;

a resilient portion extending from said first end of said dynamic reference frame positioning member; and a catch member extending transverse to said axis and outwardly from said dynamic reference frame positioning member;

wherein said first end forms a one piece bone engaging portion having a first portion and a second portion extending at a fixed angle relative to one another;

wherein the tracking sensor is tracked by the tracking system;

wherein the dynamic reference frame positioning member is operable to engage a bone in the anatomy in a selectively fixed manner;

wherein said dynamic reference frame positioning member is configured to be axially impacted along the axis of the dynamic reference frame positioning member into the bone to hold said dynamic reference frame in a selected position;

wherein said dynamic reference frame has a engaging portion defining a first cylindrical sidewall, wherein said first cylindrical sidewall defines a void though said first cylindrical sidewall and a finger extending into said void, wherein said finger selectively engages said catch member;

wherein said resilient portion biases said finger towards said catch member;

wherein said tap cap has a second cylindrical sidewall, wherein said second cylindrical sidewall defines a passage through the second cylindrical sidewall to allow said catch member to pass through said second cylindrical sidewall so that a surface of the tap cap is operable to engage the bias member while the catch member is free of said second cylindrical sidewall.

\* \* \* \* \*